(12) United States Patent
Han et al.

(10) Patent No.: US 7,737,286 B2
(45) Date of Patent: Jun. 15, 2010

(54) α-HYDROXY-BENZENEACETIC ACID DERIVATIVES, AND COMPOUNDS HAVING TWO 5-MEMBERED LATONE RINGS FUSED TO CENTRAL CYCLOHEXA-1,4-DIENE NUCLEUS BASED UPON THE SAME, AND USES OF THE COMPOUNDS

(75) Inventors: Man-joon Han, Seoul (KR); Soon-hyun Park, Suwon-Si (KR); Jwung-rhok Kim, Suwon-Si (KR); Urs Lauk, Zurich (CH)

(73) Assignee: Kyung-In Synthetic Corporation (KR)

( * ) Notice: Subject to any disclaimer, the term of this patent is extended or adjusted under 35 U.S.C. 154(b) by 808 days.

(21) Appl. No.: 10/572,233

(22) PCT Filed: Sep. 17, 2004

(86) PCT No.: PCT/KR2004/002395

§ 371 (c)(1),
(2), (4) Date: Jan. 29, 2007

(87) PCT Pub. No.: WO2005/028409

PCT Pub. Date: Mar. 31, 2005

(65) Prior Publication Data

US 2007/0220688 A1    Sep. 27, 2007

(30) Foreign Application Priority Data

Sep. 19, 2003 (KR) .................. 10-2003-0065029
Jan. 10, 2004 (KR) .................. 10-2004-0001842

(51) Int. Cl.
C07D 307/00 (2006.01)
D06P 1/00 (2006.01)

(52) U.S. Cl. .................. 549/299; 544/171; 549/475; 549/416; 562/473; 8/636; 8/638

(58) Field of Classification Search .................. 8/636
See application file for complete search history.

(56) References Cited

U.S. PATENT DOCUMENTS

| 4,368,334 A | 1/1983 | Dales |
| 5,286,881 A | 2/1994 | Sekihachi et al. |
| 5,360,912 A | 11/1994 | Kawamura et al. |
| 5,424,455 A * | 6/1995 | Yamamoto et al. .......... 549/299 |
| 5,428,162 A | 6/1995 | Nesvadba et al. |
| 5,645,970 A | 7/1997 | Cheng et al. |
| 6,359,172 B1 | 3/2002 | Kessels |

FOREIGN PATENT DOCUMENTS

| GB | 1 576 331 | 10/1980 |
| GB | 2 068 402 | 8/1981 |
| GB | 2 101 998 | 1/1983 |
| JP | 56-068641 | 6/1981 |
| JP | 1-120058 | 5/1989 |
| KR | 10-1996-0014044 | 10/1996 |
| KR | 10-2000-0056622 | 9/2000 |
| KR | 10-2001-0020439 | 3/2001 |

OTHER PUBLICATIONS

Beilstein Handbuch der Organischen Chemie, enlarged edition vol. System No. 1106/H410-411.

* cited by examiner

Primary Examiner—Harold Y Pyon
Assistant Examiner—Katie Hammer
(74) Attorney, Agent, or Firm—Cantor Colburn LLP

(57) ABSTRACT

The present invention provides α-hydroxy benzeneacetic acid derivatives of the formula as defined in the specification which is a precursor indispensable for synthesis of compounds having two 5-membered lactone rings fused to central cyclohexa-1,4-diene nucleus, and a process of easily preparing the same. According to the preparation process of the present invention, the α-hydroxy benzeneacetic acid derivative can be readily prepared at high purity and yield without using toxic materials or producing toxic by-products. Some novel compounds, synthesized by using such a α-hydroxy benzeneacetic acid derivative, have excellent fastness properties, dye fixing rate and leveling property to general synthetic fiber materials such as polyester fibers and their blends with other fibers, especially to micro fibers, and also can be used as a coloring agent for plastic resins, color tonors, color filters, etc.

10 Claims, No Drawings

α-HYDROXY-BENZENEACETIC ACID DERIVATIVES, AND COMPOUNDS HAVING TWO 5-MEMBERED LATONE RINGS FUSED TO CENTRAL CYCLOHEXA-1,4-DIENE NUCLEUS BASED UPON THE SAME, AND USES OF THE COMPOUNDS

FIELD OF THE INVENTION

The present invention relates to new α-hydroxy-benzeneacetic acid derivatives, compounds having two 5-membered lactone rings fused to central cyclohexa-1,4-diene nucleus based upon the above derivatives, and uses of these compounds. According to the present invention, there is also provided a process in which the compounds having two 5-membered lactone rings fused to central cyclohexa-1,4-diene nucleus can be readily produced without using or producing toxic materials.

BACKGROUND OF THE INVENTION

Dye compounds as represented in the below formula (hereinafter, sometimes referred to as "benzodifuranone-based dye compound"), having two 5-membered lactone rings fused to central cyclohexa-1,4-diene nucleus, have good fastness properties such as washing fastness and sublimation fastness, whereby they are generally employed in dyeing of high functionality fiber materials such as leisure- and sports-ware. However, many prior art benzodifuranone-based compounds fail to provide satisfactory properties in dyeing of some synthetic fiber materials, especially micro fibers. In other words, these benzodifuranone-based compounds exhibit a low dyeability and fastness to micro fibers.

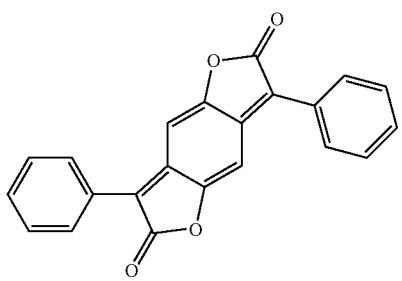

Examples of these benzodifuranone-based compounds are disclosed in U.S. Pat. No. 5,286,881, Korean Patent No. 138, 255, etc., and α-hydroxy benzeneacetic acid as represented in the below formula acid is used as a precursor indispensable for synthesis of the benzodifuranone-based compounds.

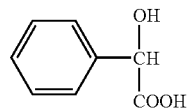

In connection with the preparation process of this α-hydroxy benzeneacetic acid (or nitrile compound thereof), there are U.S. Pat. No. 4,368,334, U.S. Pat. No. 6,359,172, British Patent No. 1,576,331, Japanese Laid-open Patent No. S56-68641, etc. In these prior art processes, α-hydroxy benzeneacetic acid is produced using phenol and glyoxylic acid.

As a process for introduction of short alkoxy group to the above α-hydroxy benzeneacetic acid, British Laid-open Patent No. 2,101,998A shows a technology of condensing the mandelic acid with propyl bromide with the aid of sodium hydroxide in water. However, in accordance with this process, the condensation reaction must be run at low temperature for a long time due to the low boiling point of propyl bromide, and also propyl bromide must be continuously added to the reaction procedure so as to replace the amount of propyl bromide lost, and the synthesized compound is produced in the form of cake, which makes a high purity and yield difficult to achieve. If alkoxy bromide with a high boiling point is employed in the above reaction, the reaction temperature must be adjusted to high temperature to maintain an acceptable reaction rate, resulting in the decomposition of α-hydroxy benzeneacetic acid under the acid or alkali conditions.

In order to solve these problems, alternative approaches, as shown in Beilstein Handbuch der Organischen Chemie, enlarged edition Vol. System No. 1106/H410-411, Japanese Laid-open Patent No. S64-120058, and Korean Laid-open Patent No. 1995-18310, were developed whereby a substitute group is first introduced to hydroxyl benzaldehyde and the resulting compound is reacted with sodium hydrogensulfite and sodium cyanide, then hydrolyzed to produce a nitrile compound, which is briefly illustrated in the below reaction formula.

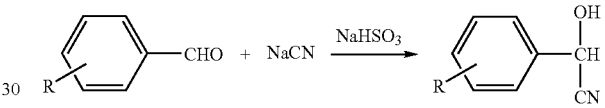

wherein R is as defined in Japanese Laid-open Patent No. S64-120058.

However, this process has drawbacks that the yield is very low at 50~81% and an expensive apparatus is required to collect toxic hydrogen cyanide gas created by the reaction, and there is a possibility of water contamination resulting from toxic cyanide. Korean Laid-open Patent No. 1996-14044 suggests a process using cyanuric chloride in place of sodium hydrogen sulfite, as illustrated in the below reaction formula.

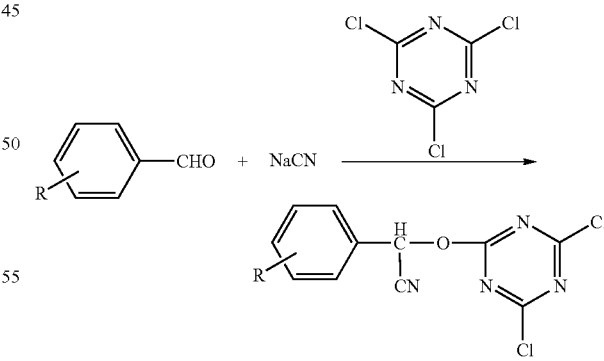

wherein R is as defined in Korean Laid-open Patent No. 1996-14044.

However, this process also has the same drawbacks as in the above process. Accordingly, there is a strong need for a novel process to effectively synthesize O-hydroxy benzeneacetic acid (including its derivatives) as an important precursor for synthesis of benzodifuranone-based compounds.

SUMMARY OF THE INVENTION

The first object of the present invention is to provide a process of easily preparing an O-hydroxy benzeneacetic acid derivative as a precursor indispensable for synthesis of benzodifuranone-based dye compounds at high purity and yield without using toxic materials or producing toxic materials as by-products in the reaction procedure.

The second object of the present invention is to provide an α-hydroxy benzeneacetic acid derivative which can be prepared by known processes or by the above process. The O-hydroxy benzeneacetic acid derivative thus prepared includes novel compounds not known yet.

The third object of the present invention is to provide a process for synthesize of benzodifuranone-based dye compounds using the α-hydroxy benzeneacetic acid derivative.

The fourth object of the present invention is to provide benzodifuranone-based dye compounds which can be prepared by known processes or by the above process. The benzodifuranone-based dyes thus prepared include novel compounds not known yet.

The fifth object of the present invention is to provide a method of dyeing hydrophobic fiber materials such as polyester fibers, polyester micro fibers, their blends with other fibers, hydrophobic fiber-based weave cloths, etc., using the above new benzodifuranone-based dye compounds or compositions thereof to provide excellent dyeability, fastness properties and leveling property to these fiber materials.

The sixth object of the present invention is to provide methods of dyeing fiber materials using the above new benzodifuranone-based dye compounds or compositions thereof together with other color dye compounds having a high fastness property to provide excellent dyeability, fastness properties and leveling property to these fiber materials. In accordance with the methods in the fifth and sixth objects, dyed products with good properties in high-grade clothes, particularly, sports-ware, new synthetic micro fibers, etc., requiring high fastness properties, can be obtained through an environmental friendly procedure. The sixth object of the present invention include the new mixtures of the above new benzodifuranone-based dye compounds and other dyes, especially disperse dyes.

The seventh object of the present invention is to provide uses of the above benzodifuranone-based dye compound and composition thereof as a coloring agent for polymer resins, color tonors or color filters.

To accomplish the foregoing objects and advantages, the present invention provides a process for preparation of the α-hydroxy benzeneacetic acid derivative as represented in Formula (I) below.

FORMULA I wherein

A is hydrogen, halogen, substituted or unsubstituted $C_1$-$C_6$ alkyl, or substituted or unsubstituted $C_1$-$C_6$ alkoxy group;

$D_1$ is —O—, —S—, —$SO_2$— or —N(—$R_2$)—, wherein $R_2$ is hydrogen, or substituted or unsubstituted $C_1$-$C_6$ alkyl group, $R_2$ is preferred hydrogen or unsubstituted $C_1$-$C_4$alkyl;

$R_1$ is hydrogen, substituted or unsubstituted $C_1$-$C_6$ alkyl, substituted or unsubstituted $C_4$-$C_7$ cyclic or heterocyclic group, substituted or unsubstituted aromatic group, or $$-(\underset{Y_1}{\overset{X_1}{C}})_{n_1}-D_2-(\underset{Y_2}{\overset{X_2}{C}})_{n_2}-D_3-(\underset{Y_3}{\overset{X_3}{C}})_{n_3}-D_4-(\underset{Y_4}{\overset{X_4}{C}})_{n_4}-Z_1,$$

wherein $D_2$, $D_3$ and $D_4$ are each independently a direct bond, —O—, —S— or —N(—$R_2$)—, wherein $R_2$ is the same as above;

$X_1$, $X_2$, $X_3$, $X_4$, $Y_1$, $Y_2$, $Y_3$ and $Y_4$ are each independently hydrogen, halogen, or substituted or unsubstituted $C_1$-$C_6$ alkyl group;

$Z_1$ is hydrogen, substituted or unsubstituted $C_1$-$C_6$ alkyl, substituted or unsubstituted $C_4$-$C_7$ cyclic or heterocyclic group, or substituted or unsubstituted aromatic group;

$n_1$ is an integer of 1~6;

$n_2$ to $n_4$ are each independently 0 or an integer of 1~6, provided that when $n_2$ is 0, at least one of $D_2$ and $D_3$ is a direct bond; when $n_3$ is 0, at least one of $D_3$ and $D_4$ is a direct bond, and when $n_2$ and $n_3$ are simultaneously 0, $D_3$ is a direct group and also at least one of $D_2$ and $D_4$ is a direct bond.

Some terms used in the present disclosure are briefly explained below.

When the term "substituted" is used without any separate or additional descriptions in the present disclosure, it means that a substituent group(s) may be covalently bonded to the primary molecule. The substituent group(s) is (are) one or more group(s) individually and independently selected from halogen, hydroxy, carboxyl, amino, sulfonyl, nitro, $C_1$-$C_6$ alkyl, $C_1$-$C_6$ alkylcarbonyloxy, $C_1$-$C_6$ alkoxy carbonyl, benzoyl vinyl, and the like.

The term "halogen" refers to fluoride, chloride, bromide, etc.

The term "$C_1$-$C_6$ alkyl group" refers to methyl, ethyl, propyl, butyl, isopropyl, pentyl, isobutyl, hexyl, isopentyl, isohexyl and the like.

The term "$C_1$-$C_6$ alkoxy group" refers to methoxy, ethoxy, n-propoxy, isopropoxy, n-butoxy, isobutoxy, t-butoxy, n-pentyloxy, n-hexyloxy and the like.

The term "$C_4$-$C_7$ cyclic group" refers to cyclobutyl, cyclopentyl, cyclohexyl and the like.

The term "heterocyclic group" includes, for example, but is not limited to thienyl, pyrolyl, pyranyl, thiazolyl, oxazolyl, pyrazolyl, imidazolyl, thiadiazolyl, thiadiazolyl, s-triazinyl, benzofuranyl, benzothienyl, indolyl, benzoxazolyl, benzimidazolyl, benzothiazolyl, etc.

The term "aromatic group" refers to phenyl, naphthyl and the like.

The term "$C_1$-$C_6$alkylcarbonyloxy" refers to acetoxy, propionyloxy, n-butyryloxy and the like.

The term "$C_1$-$C_6$ alkoxycarbonyl" refers to methoxycarbonyl, ethoxycarbonyl, n-propoxycarbonyl, isopropoxycarbonyl and the like.

One skilled in the art to which the present invention pertains would readily appreciate the meaning of other terms used in the present disclosure.

A process for preparation of an α-hydroxy benzeneacetic acid derivative according to the present invention comprises a step of reacting an benzaldehyde derivative as represented in Formula (II) below with the aid of a phase transfer catalyst in a two-phase solvent system of an organic reactant solvent capable of releasing a carbene upon treatment with alkali salt and a basic aqueous solvent, both solvents being not mixed with each other, to synthesize the α-hydroxy benzeneacetic acid derivative of Formula (I).

Formula II

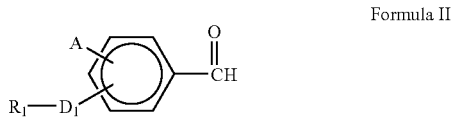

wherein A, $D_1$ and $R_1$ are the same as in Formula I.

The two-phase solvent system of an organic reactant solvent and basic aqueous solvent, both solvents being not mixed with each other, consists of an organic layer of organic solvent and an aqueous layer of aqueous solvent. Therefore, the benzaldehyde derivative of Formula (II) reacts while being exchanged between the organic layer and aqueous layer to be converted into the compound of Formula (I) due to the functioning of a phase transfer catalyst.

The organic reactant solvent includes, for example, but is not limited to chloroform ($CHCl_3$), dichloromethane ($CH_2Cl_2$), etc. Of them, chloroform is particularly preferred.

Alkali salts contained in the basic aqueous solvent include, for example, but are not limited to strong alkali salts such as KOH, NaOH, LiOH, etc. and weak alkali salts such as $Na_2CO_3$, $NaHCO_3$, etc. Of them, the strong alkali salts are more preferred. The concentration of alkali salt can be determined considering the amount of benzaldehyde derivative of Formula (II) as a reactant, the ratio of both solvents and the like, and is preferably in the range of 1~20 M (molar amount).

The ratio of both solvent layers is desirably in the range of 1:10~10:1 by volume for appropriate performance of the phase transfer catalytic reaction.

The phase transfer catalyst includes, for example, but is not limited to benzyltriethylammonium chloride, tetrabutylammonium chloride, benzyltributylammonium chloride, etc. The addition amount of the phase transfer catalyst depends upon several reaction parameters such as the concentration of benzaldehyde derivative as a reactant, the amount of both solvent layers and the like, thus the amount is not particularly limited so long as it is in the range of inducing a reaction.

The reaction is desirably carried out at 30~80° C. for 1~4 hours.

In a preferable embodiment, a reaction system after the phase transfer catalyst reaction is acidified so that —COONa bonded to an aromatic ring of a product is converted into —COOH. Moreover, by acidification of the reaction system, the organic layer and aqueous layer are distinctively separated whereby the organic layer, containing most of α-hydroxy benzeneacetic acid derivatives of Formula (I), can be further easily partitioned. The acidification of reaction system can be achieved by adding acidic compounds such as hydrochloric acid, sulfuric acid, nitric acid, phosphoric acid, etc. thereto. The preferable acidity of reaction system is pH 2 or less, and more preferably pH 1 or less.

In a more preferable embodiment, in order to improve the separation of both solvent layers, a nonpolar compound (solvent), not affecting reactants and reaction, can be further added to a reaction system after the phase transfer catalyst reaction. This nonpolar compound includes, for example, but is not limited to o-dichlorobenzene, monochlorobenzene, chloroform, dichloromethane, dichloroethane, benzene, bromobenzene, nitrobenzene, toluene, xylene, trichloroethylene, ethyl isobutyl ketone, acetic acid, etc. As the nonpolar compound is added to the reaction system, the separation of layers is accelerated, as described above, and also some products (α-hydroxy benzeneacetic acid derivatives) contained in an aqueous layer moves to an organic layer, thereby increasing the yield of products. The addition amount of the nonpolar compound is not particularly limited so long as the above effect can be obtained, and is in the range of 5~200% based upon the entire volume of both solvents in the 2-phase solvent system.

The benzaldehyde derivative of Formula (II), which is a starting material for the above process, can be synthesized by well-known methods. For instance, alkyl or heterocyclic alkyl carbitol chloride is added to hydroxyl benzaldehyde, then a reaction catalyst such as potassium bromide, sodium bromide, potassium iodide or sodium iodide is added thereto at a final concentration of 1~4 M, followed by incubating at 90~160° C. for 2~18 hours to synthesize the derivative of Formula (II).

For the purpose of helping the understanding of the above phase transfer catalyst reaction, Reaction formula (1) below is provided in which sodium hydroxide-containing water is used as an aqueous layer and chloroform is used as an organic layer, and also in which a mechanism of producing the α-hydroxy benzeneacetic acid derivative of Formula (I) is illustrated; however, this mechanism is just an anticipated mechanism and not intended to restrict the spirit and scope of the present invention.

Reaction Formula 1

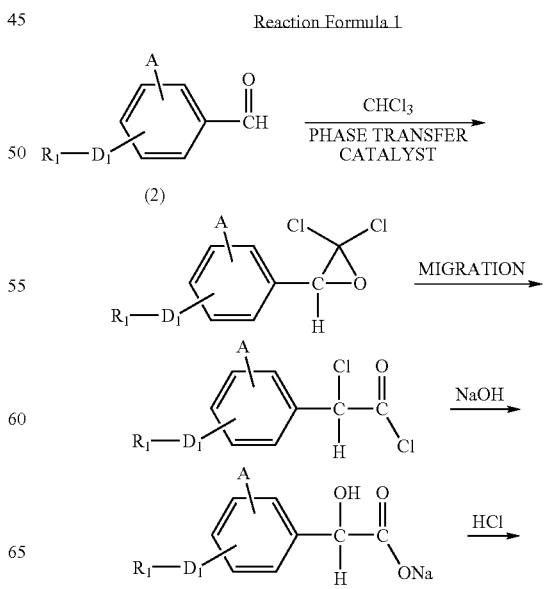

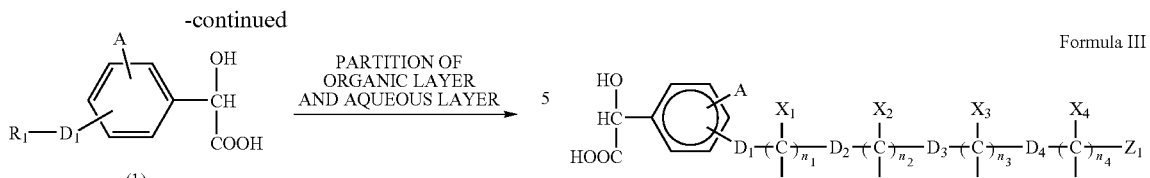

In a preferable embodiment, in order to increase the efficiency of process, immediately before partition of both layers, one or more steps selected from the group consisting of benzoylation, cyanylation, acetylation, propylation, maleylation, benzenesulfonylation, alkylbenzenesulfonylation and alkylcarbonylation may be further performed.

The above preparation process of α-hydroxy benzeneacetic acid derivative according to the present invention is characterized in that no toxic materials such as cyanide are used and also no toxic by-products such as hydrogen cyanide gas are produced, and that the desired product can be produced at high purity and yield. Moreover, in the prior art preparation processes, the α-hydroxy benzeneacetic acid derivative is obtained in a form of crystals, thereby requiring the recovery of the derivative from a reaction, which is furthermore a difficult procedure. Relative to these prior art processes, in the preparation process of the present invention, the α-hydroxy benzeneacetic acid derivative is obtained in an aqueous form, thus it can be subsequently used in a procedure for synthesis of the benzodifuranone-based dye compounds without any recovery step, resulting in the increased yield of a final product.

The present invention also provides an α-hydroxy benzeneacetic acid derivative which can be obtained by known processes or by the above preparation process. As already mentioned above, the o-hydroxy benzeneacetic acid derivative is used as an indispensable precursor in the preparation process of benzodifuranone-based dye compounds.

Especially, a compound (a) in which $R_1$ is

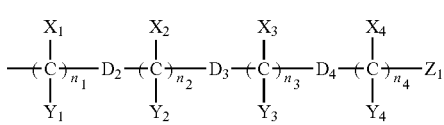

in Formula 1 wherein $Z_1$ is cyclic or heterocyclic group or aromatic group and a compound (b) in which $R_1$ is

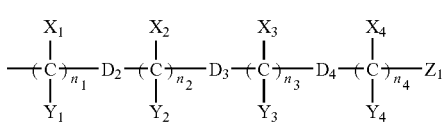

in Formula 1 wherein all of $n_2$, $n_3$ and $n_4$ are not 0, respectively, are novel compounds not known yet. These novel compounds are an object of the present invention. They are represented as Formula III below.

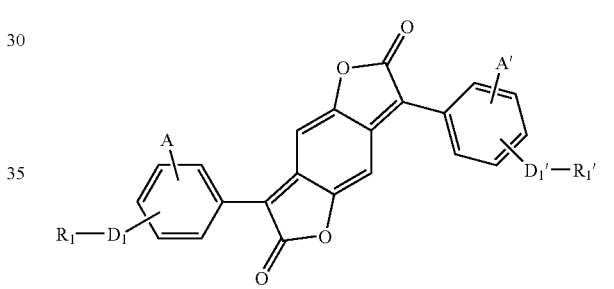

wherein $A, D_1, D_2, D_3, D_4, X_1, X_2, X_3, X_4, Y_1, Y_2, Y_3, Y_4$ and $n_1$ are the same as in Formula 1;

$n_2$ to $n_4$ are each independently 0 or an integer of 1~6, and $Z_1$ is substituted or unsubstituted $C_4$-$C_7$ cyclic or heterocyclic group, or substituted or unsubstituted aromatic group; or $n_2$ to $n_4$ are each independently an integer of 1~6, and $Z_1$ is hydrogen, substituted or unsubstituted $C_1$-$C_6$ alkyl, substituted or unsubstituted $C_4$-$C_7$ cyclic or heterocyclic group, or substituted or unsubstituted aromatic group.

The present invention also provides a process for preparation of the benzodifuranone-based dye compounds as represented in Formula (IV) below using the α-hydroxy benzeneacetic acid derivative of Formula (I).

Formula IV

[Structure of benzodifuranone-based dye compound]

wherein

A, $D_1$ and $R_1$ are the same as in Formula I;

A' is hydrogen, halogen, substituted or unsubstituted $C_1$-$C_6$ alkyl, or substituted or unsubstituted $C_1$-$C_6$ alkoxy group;

$D_1'$ is a direct bond, —O—, —S—, —SO$_2$— or —N(—R$_2$)—, wherein $R_2$ is hydrogen, or substituted or unsubstituted $C_1$-$C_6$ alkyl group;

$R_1'$ is hydrogen, substituted or unsubstituted $C_1$-$C_6$ alkyl, substituted or unsubstituted $C_4$-$C_7$ cyclic or heterocyclic group, substituted or unsubstituted aromatic group, or

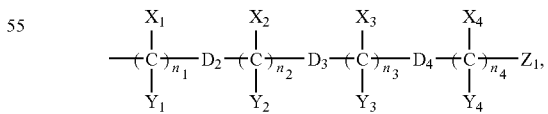

wherein $D_2$, $D_3$ and $D_4$ are each independently a direct bond, —O—, —S— or —N(—R$_2$)—, wherein $R_2$ is the same as above;

$X_1, X_2, X_3, X_4, Y_1, Y_2, Y_3$ and $Y_4$ are each independently hydrogen, halogen, or substituted or unsubstituted $C_1$-$C_6$ alkyl group;

$Z_1$ is hydrogen, substituted or unsubstituted $C_1$-$C_6$ alkyl, substituted or unsubstituted $C_4$-$C_7$ cyclic or heterocyclic group, or substituted or unsubstituted aromatic group;

$n_1$ is an integer of 1~6;

$n_2$ to $n_4$ are each independently 0 or an integer of 1~6, provided that when $n_2$ is 0, at least one of $D_2$ and $D_3$ is a direct bond; when $n_3$ is 0, at least one of $D_3$ and $D_4$ is a direct bond; and when $n_2$ and $n_3$ are simultaneously 0, $D_3$ is a direct group and also at least one of $D_2$ and $D_4$ is a direct bond.

More specifically, the benzodifuranone-based dye compounds of Formula (IV) can be produced by a process comprising a step of condensation of the α-hydroxy benzeneacetic acid derivative of Formula (I) and a compound as represented in Formula (V) below by an acid catalyst in an organic solvent, followed by oxidation.

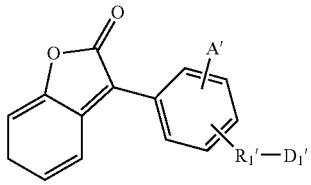

Formula V wherein A', $R_1$' and $D_1$' are the same as defined in Formula (IV).

The organic solvent as defined in the above process includes, for example, but is not limited to benzene, toluene, o-xylene, p-xylene, dichlorobenzene, bromobenzene, chloronaphthalene, 1,2-dichloroethane, 1,1,1-trichloroethane, 1,1,2,2-tetrachloroethane, trichloroethylene, dichloromethane, chloroform, nitrobenzene, methyl isobutyl ketone, acetic acid, etc. In some embodiments, a mixed solvent of two or more selected from the above organic solvents may be used. In other embodiments, a mixed solvent may be used whereby sulfuric acid and/or benzene-based organic acid are added at 0.5~50% based upon the entire volume of the mixed solvent to the above organic solvent.

The acid catalyst for the condensation reaction as defined in the above process includes, for example, but is not limited to sulfuric acid, benzenesulfonic acid, benzenemethanedisulfonic acid, methanesulfonic acid, trifluoroacetic acid, titanium tetrachloride, ammonium chloride, ferric chloride, boron chloride, hydrogen chloride, etc. The addition amount of the catalyst is not particularly limited but can be determined in the range of accelerating the condensation reaction while not affecting a product.

The reaction temperature for condensation is preferred to be approximately 50~150° C., more preferably 70~115° C., and the reaction time therefor is approximately 5~20 hours.

As can be seen in the above reaction conditions, the condensation reaction is rapidly run at relatively low temperature, thus side reactions as well as the decomposition of a product are restricted to allow the benzodifuranone-based dye compound of Formula (IV) to be produced at high purity and yield.

The oxidation reaction as defined in the above process can be preferably carried out for a short time using an oxidant Examples of such oxidant include, but are not limited to, sodium thiosulfate, sodium nitrite, 10% sodium hypochloride, 10% potassium hypochloride, sodium chlorite, sodium perchlorate, potassium permanganate, nitrobenzene, dicyanochloro benzoquinone, 30% hydrogen peroxide, chloranil, etc. The addition amount of the oxidant can be determined in the range of accelerating the oxidation reaction while not affecting a product.

After completion of the oxidation, the synthesized product is added to a solvent such as water, methanol and the like, or conversely the solvent is poured into a reaction containing the synthesized product, whereby the benzodifuranone-based dye compound as a synthesized product can be obtained in a crystalline phase.

The mixing ratio of the α-hydroxy benzeneacetic acid derivative of Formula (I) and the compound of Formula (V) is desirably in the range of 1:10~10:1 by equivalent.

The compound of Formula (V) can be produced by a process comprising condensation of the α-hydroxy benzeneacetic acid derivative of Formula (I), wherein A, $D_1$ and $R_1$ are replaced with A, $D_1$' and $R_1$', respectively, and hydroquinone in sulfuric acid or a mixed solvent of sulfuric acid and acetic acid, followed by oxidation, which is illustrated in Reaction formula (2) below.

Reaction Formula 2

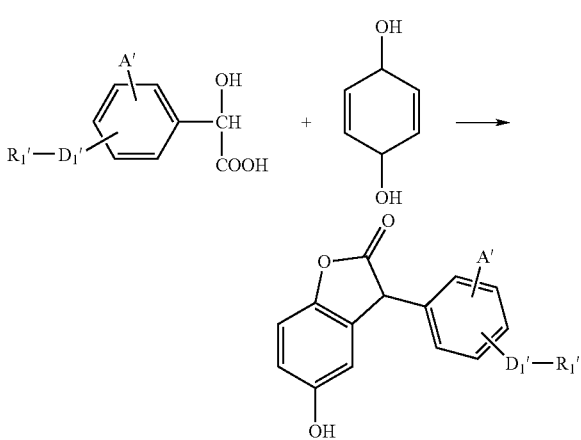

The condensation reaction described in the above process can be performed by well-known methods in the art to which the present invention pertains, for example, in 50~80% sulfuric acid solution at 70~110° C.

The present invention also provides the new benzodifuranone-based dye compound of Formula IV which can be produced by the above preparation process.

Especially, compounds of Formula (IV)

(IV)

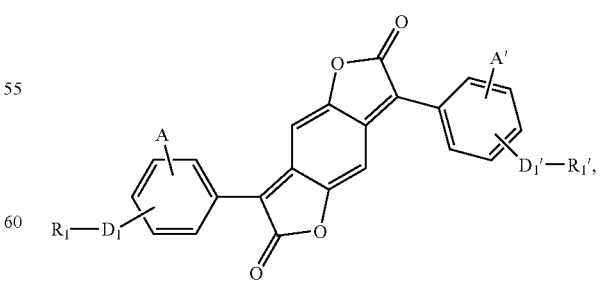

wherein

A is hydrogen, halogen, substituted or unsubstituted $C_1$-$C_6$ alkyl, or substituted or unsubstituted $C_1$-$C_6$ alkoxy group;

$D_1$ is —O—, —S—, —SO$_2$— or —N(—R$_2$)—, wherein R$_2$ is hydrogen, or substituted or unsubstituted C$_1$-C$_6$ alkyl group;

R$_1$ is

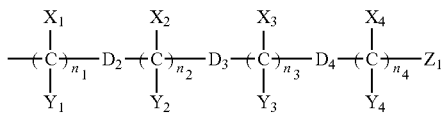

wherein

D$_2$ and D$_3$ are each independently —O—, —S— or —N(—R$_2$)—, wherein R$_2$ is the same as above;

D$_4$ is a direct bond, —O—, —S— or —N(—R$_2$), wherein R$_2$ is the same as above;

X$_1$, X$_2$, X$_3$, X$_4$, Y$_1$, Y$_2$, Y$_3$ and Y$_4$ are each independently hydrogen, halogen, or substituted or unsubstituted C$_1$-C$_6$ alkyl group;

Z$_1$ is substituted or unsubstituted C$_3$-C$_6$ alkyl, substituted or unsubstituted C$_4$-C$_7$ cyclic or heterocyclic group, or substituted or unsubstituted aromatic group;

n$_1$ to n$_3$ are an integer of 1~6; n$_4$ is 0 or an integer of 1~6;

A' is hydrogen, halogen, substituted or unsubstituted C$_1$-C$_6$ alkyl, or substituted or unsubstituted C$_1$-C$_6$ alkoxy group;

D$_1$' is a direct bond, —O—, —S—, —SO$_2$— or —N(—R$_2$)—, wherein R$_2$ is hydrogen, or substituted or unsubstituted C$_1$-C$_6$ alkyl group;

R$_1$' is hydrogen, substituted or unsubstituted C$_1$-C$_6$ alkyl, substituted or unsubstituted C$_4$-C$_7$ cyclic or heterocyclic group, substituted or unsubstituted aromatic group, or

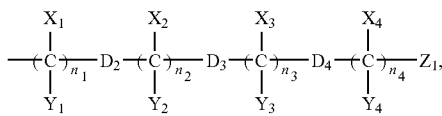

wherein

D$_2$, D$_3$ and D$_4$ are each independently a direct bond, —O—, —S— or —N(—R$_2$)—, wherein R$_2$ is the same as above;

X$_1$, X$_2$, X$_3$, X$_4$, Y$_1$, Y$_2$, Y$_3$ and Y$_4$ are each independently hydrogen, halogen, or substituted or unsubstituted C$_1$-C$_6$ alkyl group;

Z$_1$ is hydrogen, substituted or unsubstituted C$_1$-C$_6$ alkyl, substituted or unsubstituted C$_4$-C$_7$ cyclic or heterocyclic group, or substituted or unsubstituted aromatic group;

n$_1$ is an integer of 1~6;

n$_2$ to n$_4$ are each independently 0 or an integer of 1~6, provided that when n$_2$ is 0, at least one of D$_2$ and D$_3$ is a direct bond; when n$_3$ is 0, at least one of D$_3$ and D$_4$ is a direct bond; and when n$_2$ and n$_3$ are simultaneously 0, D$_3$ is a direct bond and also at least one of D$_2$ and D$_4$ is a direct bond, are novel compounds not known yet.

These novel benzodifuranone-based compounds provide excellent fastness properties, dyeability and leveling property when used as dyes for synthetic fibers such as polyester fibers and their blends with other fibers, and especially, micro fibers.

Moreover, the novel benzodifuranone-based compounds are distinguished by very good build-up capacity and low degree of contact discoloration (staining).

More preferably, the novel compounds of formula (IV) as described above, wherein D$_1$, D$_2$ and D$_3$ are —O—, were ascertained to exhibit prominent dyeing properties (dye fixing rate, leveling property) and, particularly fastness properties unexpectable in a prior art, through experiments carried out by the inventors of the present invention.

Preferred compound of the formula (IV) are those, wherein A' is hydrogen, D$_1$' is a direct bond, R$_1$' is hydrogen, and A, D$_1$ and R$_1$ have the meanings given under formula (IV).

Further preferred benzodifuranone-based compounds of formula (IV) are those wherein D$_4$ is a direct bond, n$_4$ is 0 and Z$_1$ denotes C$_3$-C$_6$alkyl. Especially preferred are the benzodifuranone-based compounds of formula (IV), wherein A is hydrogen, D$_1$, D$_2$, and D$_3$ are —O—, D$_4$ is a direct bond, n$_4$ is 0 and Z$_1$ is C$_3$-C$_6$alkyl, A' is hydrogen, D$_1$' is a direct bond and R$_1$' is hydrogen.

More preferred benzodifuranone-based compounds of formula (IV) are those wherein n$_1$ and n$_2$ are 2. Especially preferred are the benzodifuranone-based compounds of formula (IV), wherein A is hydrogen, D$_1$, D$_2$, and D$_3$ are —O—, D$_4$ is a direct bond, n$_4$ is 0 and Z$_1$ is C$_3$-C$_6$ alkyl, n$_1$ and n$_2$ are 2 and X$_1$, X$_2$, X$_3$, Y$_1$, Y$_2$ and Y$_3$ are hydrogen, A' is hydrogen, D$_1$' is a direct bond and R$_1$' is hydrogen.

Compounds of formula (IV) wherein n$_3$ is 1, D$_4$ is a direct bond, n$_4$ is 0 and Z$_1$ denotes n-propyl, are particularly preferred, especially wherein n$_1$ and n$_2$ are 2, n$_3$ is 1, D$_1$, D$_2$ and D$_3$ are —O—, D$_4$ is a direct bond, n$_4$ is 0, Z$_1$ is n-propyl, A and A' are hydrogen, D$_1$' is a direct bond and R$_1$' is hydrogen.

Generally, micro fibers have a large surface area per weight so that they are difficult to dye to a desired high concentration dyeing using a small quantity; for example, even where dye compounds of 3~5 times larger quantity are used, only about ½ time dyeing concentration can be obtained in a dyed product. On the other hand, the benzodifuranone-based dye compounds (a, b and c) having the chain structure as described above were ascertained to exhibit excellent effects on dyeing of hydrophobic fibers, especially, micro fibers, their blends with other fibers, and polyester blend fibers, whereby a high dyeing concentration can be achieved even when a small amount of dye compounds is used, thus they can be used as environmental friendly dyes by significantly reducing the amount of waste water generated on dyeing.

Another object of the present invention is to provide the mixture of the benzodifuranone-based compound according to the present invention together with other dyes useful for dyeing hydrophobic fibers. These other dye compounds, which are useful in dyeing hydrophobic fibers and provide a good washing fastness, include, for example, but are not limited to anthraquinone-based compounds, azo-based compounds, the compounds as represented in Formulas VI to XII below. These dye compounds may also be used in a combination of 2 or more. These dye compounds can be used at an amount of 1 to 99% based upon the entire weight of the mixture with the benzodifuranone-based compound according to the present invention. The following dyes formulae (VI) to (XII) can be used in combination with the benzodifurane-based dye compound of formula (IV), especially the new benzodifurane-based dye compounds of formula (IV).

Formula VI

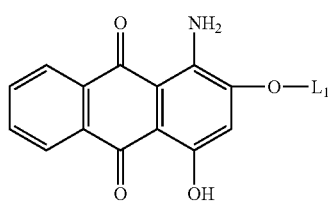

wherein L$_1$ is C$_1$-C$_6$ alkyl, phenyl, or C$_1$-C$_4$ alkoxyphenylsulfonyl group.

Formula VII wherein $P_1$ and $P_2$ are each independently $C_1$-$C_6$ alkyl, phenyl, $C_1$-$C_4$ alkoxyphenylsulfonyl, cyanoethyl, cyanopropyl, phenoxyethyl, $C_1$-$C_6$ alkoxyethyl or alkoxypropyl, or $C_1$-$C_6$ alkoxy carbitoxy group;

$P_3$ and $P_4$ and $Q_1$, $Q_2$ and $Q_3$ are each independently hydrogen, $C_1$-$C_4$ alkyl, especially methyl, hydroxy, acetyl amide, propionyl amide, butylcarbonyl amide, $C_1$-$C_4$ alkoxy, nitro or a cyano group.

Formula VIII wherein $R_{10}$ is $C_1$-$C_6$ alkyl, especially $C_1$-$C_4$ alkyl;

$R_{11}$ and $R_{12}$ are each independently hydrogen, cyano or halogen, especially chlorine or bromine;

$R_{13}$ is $C_1$-$C_4$ alkyl, especially methyl or ethyl, hydroxy, halogen, especially bromine or chlorine, —NH—SO$_2$—$R_{16}$ or —NH—CO—$R_{17}$, wherein $R_{16}$ is $C_1$-$C_4$ alkyl, and $R_{17}$ is $C_1$-$C_4$ alkyl or $C_1$-$C_4$alkoxy-$C_1$-$C_4$ alkyl; and $R_{14}$ and $R_{15}$ independently of one another are $C_1$-$C_6$ alkyl which is unsubstituted or substituted by one or more hydroxy groups, halogen atoms, $C_1$-$C_4$ alkoxy groups, $C_2$-$C_8$ alkoxy-alkoxy groups, $C_1$-$C_4$alkyl-COO— groups or $C_1$-$C_4$alkyl-OCO— groups.

In preferred mixtures, a dye of the formula VIII is used, wherein $R_{10}$ is $C_1$-$C_4$ alkyl, especially methyl, ethyl or n-propyl, $R_{11}$ and $R_{12}$ independently of one another are hydrogen, bromine or cyano, $R_{13}$ is —NH—CO—$R_{17}$, wherein $R_{17}$ is methyl or ethyl, and $R_{14}$ and $R_{15}$ are ethyl or methoxyethyl.

In very preferred dyes of the formula (VIII), $R_{10}$ is methyl, ethyl or butyl, $R_{11}$ is hydrogen, cyano or bromine, $R_{12}$ is bromine or cyano, $R_{13}$ is acetylamino and $R_{14}$ and $R_{15}$ are $C_1$-$C_3$alkyl or methoxyethyl.

Formula IX wherein $R_{18}$ and $R_{19}$ are each independently hydrogen, $C_1$-$C_6$ alkyl, especially methyl, ethyl or butyl, $C_1$-$C_6$alkoxy, especially methoxy, ethoxy and n-propoxy, $C_1$-$C_4$ alkoxy-$C_1$-$C_4$ alkoxycarbonyl-$C_1$-$C_4$ alkoxy groups, or $R_{18}$ and $R_{19}$ are heterocyclyl-$C_1$-$C_4$ alkoxy groups, especially tetrahydrofuranyl-$C_1$-$C_4$ alkoxy groups.

In preferred dyes of formula (IX), one of $R_{18}$ or $R_{19}$ is not hydrogen.

In very preferred dyes of formula (IX), one of $R_{18}$ or $R_{19}$ is hydrogen and the other substituents $R_{19}$ or $R_{18}$ is $C_1$-$C_3$ alkoxy, $C_1$-$C_3$ alkoxy-$C_1$-$C_3$ alkoxy-carbonyl-$C_1$-$C_2$ alkoxy.

Formula X wherein $R_{20}$ and $R_{21}$ are each independently hydrogen, halogen, especially chlorine or bromine, or cyano;

$R_{22}$ is $C_1$-$C_6$alkyl, especially methyl, nitro or $C_1$-$C_4$ alkoxy;

$R_{23}$ and $R_{24}$ are each independently $C_1$-$C_6$ alkyl or $C_1$-$C_4$ alkoxy-$C_1$-$C_4$ alkyl; and $R_{25}$ is $C_1$-$C_4$ alkyl, especially methyl or ethyl, hydroxy, halogen, especially bromine or chlorine, —NH—SO$_2$—$R_{16}$ or —NH—CO—$R_{17}$, wherein $R_{16}$ and $R_{17}$ have the meaning given under formula VIII.

In preferred dyes of the formula (X), $R_{20}$ and $R_{21}$ are cyano, $R_{22}$ is $C_1$-$C_3$ alkyl, $R_{23}$ and $R_{24}$ are $C_2$-$C_4$ alkyl, $R_{25}$ in o-position to the azo group is —NH—SO$_2$—$R_{16}$, and $R_{16}$ is $C_1$-$C_3$ alkyl.

Formula XI wherein $R_{26}$ is $C_1$-$C_6$ alkyl, nitro or $C_1$-$C_6$ alkoxy;

$R_{27}$ is cyano, nitro or halogen, especially bromine or chlorine;

$R_{28}$ is hydrogen, cyano, nitro or halogen, especially bromine or chlorine;

$R_{29}$ is $C_1$-$C_6$ alkyl, especially methyl;

$R_{30}$ is cyano;

$R_{31}$ is $C_1$-$C_6$ alkyl, $C_1$-$C_4$ alkoxy-$C_1$-$C_4$ alkyl, phenyl-$C_1$-$C_4$ alkyl or phenoxy-$C_1$-$C_4$ alkyl; and $R_{32}$ is hydrogen or hydroxy.

In preferred dyes of the formula (XI), $R_{26}$ is $C_1$-$C_4$alkoxy, especially methoxy, $R_{27}$ is nitro, $R_{28}$ is hydrogen, $R_{29}$ is methyl, $R_{30}$ is cyano, $R_{31}$ $C_1$-$C_4$ alkyl, $C_1$-$C_4$alkoxy-$C_1$-$C_4$alkyl, and $R_{32}$ is the hydroxy group.

Formula XII

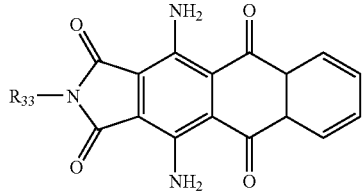

wherein $R_{33}$ is $C_1$-$C_6$ alkyl, especially $C_2$-$C_4$ alkyl, unsubstituted or substituted by $C_1$-$C_4$ alkoxy, especially $C_1$-$C_2$alkoxy, or $C_1$-$C_4$alkoxy-$C_1$-$C_4$alkoxy, especially $C_1$-$C_2$alkoxy-$C_2$-$C_3$alkoxy.

Preferred mixtures of dyes containing dyes of formula (XII) are those containing two different dyes of formula (XII), especially those wherein $R_{33}$ in one dye is a $C_1$-$C_2$alkoxy-$C_2$-$C_3$ alkyl radical, and $R_{33}$ in the other dye is a $C_1$-$C_2$ alkoxy-$C_2$-$C_3$ alkoxy-$C_2$-$C_3$alkyl radical.

A preferred embodiment of the present invention is the mixture of the dye of the formula (IV), together with at least one dye of the formulae (VI), (VII), (VIII), (IX), (X), (XI) and (XII), wherein A is hydrogen, halogen, substituted or unsubstituted $C_1$-$C_6$ alkyl, or substituted or unsubstituted $C_1$-$C_6$ alkoxy group;

$D_1$ is —O—, —S—, —SO$_2$— or —N(—R$_2$)—, wherein $R_2$ is hydrogen, or substituted or unsubstituted $C_1$-$C_6$ alkyl group;

$R_1$ is

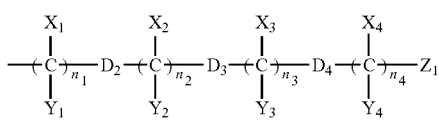

wherein $D_2$ and $D_3$ are each independently —O—, —S— or —N(—R$_2$)—, wherein $R_2$ is the same as above;

$D_4$ is a direct bond, —O—, —S— or —N(—R$_2$)—, wherein $R_2$ is the same as above;

$X_1, X_2, X_3, X_4, Y_1, Y_2, Y_3$ and $Y_4$ are each independently hydrogen, halogen, or substituted or unsubstituted $C_1$-$C_6$ alkyl group;

$Z_1$ is substituted or unsubstituted $C_3$-$C_6$ alkyl, substituted or unsubstituted $C_4$-$C_7$ cyclic or heterocyclic group, or substituted or unsubstituted aromatic group;

$n_1$ to $n_3$ are an integer of 1~6;

$n_4$ is 0 or an integer of 1~6.

A' is hydrogen, halogen, substituted or unsubstituted $C_1$-$C_6$ alkyl, or substituted or unsubstituted $C_1$-$C_6$ alkoxy group;

$D_1'$ is a direct bond, —O—, —S—, —SO$_2$— or —N(—R$_2$)—, wherein $R_2$ is hydrogen, or substituted or unsubstituted $C_1$-$C_6$ alkyl group;

$R_1'$ is hydrogen, substituted or unsubstituted $C_1$-$C_6$ alkyl, substituted or unsubstituted $C_4$-$C_7$ cyclic or heterocyclic group, substituted or unsubstituted aromatic group, or

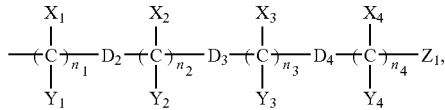

wherein $D_2, D_3$ and $D_4$ are each independently a direct bond, —O—, —S— or —N(—R$_2$)—, wherein $R_2$ is the same as above;

$X_1, X_2, X_3, X_4, Y_1, Y_2, Y_3$ and $Y_4$ are each independently hydrogen, halogen, or substituted or unsubstituted $C_1$-$C_6$ alkyl group;

$Z_1$ is hydrogen, substituted or unsubstituted $C_1$-$C_6$ alkyl, substituted or unsubstituted $C_4$-$C_7$ cyclic or heterocyclic group, or substituted or unsubstituted aromatic group;

$n_1$ is an integer of 1~6;

$n_2$ to $n_4$ are each independently 0 or an integer of 1~6, provided that when $n_2$ is 0, at least one of $D_2$ and $D_3$ is a direct bond, when $n_3$ is 0, at least one of $D_3$ and $D_4$ is a direct bond; and when $n_2$ and $n_3$ are simultaneously 0, $D_3$ is a direct bond and also at least one of $D_2$ and $D_4$ is a direct bond.

A more preferred embodiment of the present invention is the mixture of the dye of the formula (IV), wherein $D_1$, $D_2$ and $D_3$ are —O—, together with at least one dye of the formulae (VI), (VII), (VIII), (IX), (X), (XI) and (XII), especially together with at least one dye of the preferred dyes of the formulae (VI), (VII), (VIII); (IX), (XI) and (XII).

A most preferred embodiment of the present invention is the mixture of the dye of the formula (IV), wherein A and A' is hydrogen, $D_1$ is —O—, $D_1'$ is a direct bond, $R_1$ is

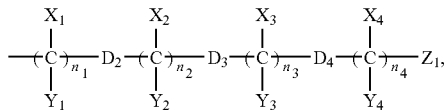

wherein $D_2$ and $D_3$ are —O—, $n_1$ and $n_2$ are 2, $n_3$ and $n_4$ are 0, $D_4$ is a direct bond and $Z_1$ is $C_3$-$C_6$alkyl, and $R_1'$ is hydrogen, together with at least one dye of the preferred dye of the formulae (VI), (VII), (VIII); (IX), (X) and (XI).

A further very preferred embodiment of the present invention is the mixture of at least one dye of the formula (IV), wherein A, A', $R_1'$, $R_1'$, $D_1$ and $D_1'$ have the meaning given for the preferred, more preferred or further preferred dyes of the formula (IV), given above, especially those, wherein A' is hydrogen, $D_1'$ is a direct bond and $R_1'$ is hydrogen and A, $D_1$ and $R_1$ have the meaning given for the preferred, further preferred and very preferred compounds, together with at least one dye of the formulae (VI), (VII), (VIII), (IX), (X), (XI) and (XII), especially the preferred dyes of the formulae (VI), (VII), (VIII), (IX), (X), (XI) and (XII).

The dye compound of the present invention can provide very light colors when used together with c.i. Yellow 184-1, Yellow 82, Orange 118, Red 362, Red 364, Red 277, etc. which are kinds of anthraquinone-based dye compounds, and also provide a variety of colors and an excellent washing fastness to polyester fibers when used together with c.i. Yellow 114, Yellow 149, Orange 148, Red 74-1, Red 360, Blue 257, Brown 19, Blue 284, Red 311, etc. which have a good washing fastness to polyester fibers.

Further, the dye compound of the present invention can provide a good washing fastness and sublimation fastness to polyester fibers and also very good fastnesses to a weave cloth thereof, when used together with Dispersol range, and/or Synolon range compounds which are kinds of azo-based dye compounds.

Further, the dye compound of the present invention can provide a good washing fastness and sublimation fastness to polyester fibers and also very good fastnesses to a weave cloth thereof, when used together with washfast disperse dyes of the Terasil range, Dispersol range, and/or Synolon range compounds which are kinds of azo-based dye compounds.

Furthermore, the benzodifuranone-based compound of Formula IV according to the present invention can be used as a coloring agent for plastic resins, color filters, color tonors and the like. In accordance with the experiments carried out by the inventors of the present invention, the compound of Formula IV has good thermostability, coloring reproducibility, etc. thereby can be applied to injection molding, spinning process, etc. and also it has an excellent property as a coloring agent for color filter or color tonor.

DETAILED DESCRIPTION OF THE PREFERRED EMBODIMENTS

Hereinafter, the present invention will be described in more detail by Examples and Experimental examples, but the scope of the present invention is not limited thereto. Hereinafter, "parts" means "parts by weight".

Example 1

22.6 parts of 4-propoxyethoxy benzaldehyde was mixed with 19.6 parts of chloroform and 2.5 parts of benzyltriethylammonium chloride and the resulting mixture was heated to about 55° C., then water containing 11 parts of sodium hydroxide was added thereto over 3 hours. The mixture was allowed to react at 55~65° C. for 2 hours. The reaction mixture was then acidified by adding 11 parts of hydrochloric acid and 40 parts of o-dichlorobenzene were added thereto, whereafter an organic layer (chloroform and o-dichlorobenzene) was partitioned to obtain 23.5 g of 4-propoxy-α-hydroxybenzeneacetic acid (yield: 93%).

Example 2

21.8 parts of 4-butoxyethoxy benzaldehyde was mixed with 19.6 parts of chloroform and 2.5 parts of benzyltriethylammonium chloride and the resulting mixture was heated to about 57° C., then water containing 11 parts of sodium hydroxide was added thereto over 4 hours. The mixture was allowed to react at 5540° C. for 2 hours. The reaction mixture was then acidified by adding 11 parts of hydrochloric acid and 30 parts of chloroform were added thereto, whereafter an organic layer (chloroform) was partitioned to obtain 21.1 g of 4-butoxy-α-hydroxy benzeneacetic acid (yield: 95%).

Example 3

35 parts of 4-tetrahydroxyperfuryloxycarbitol benzaldehyde was mixed with 19.6 parts of chloroform and 2.5 parts of benzyltriethylammonium chloride and the resulting mixture was heated to about 57° C., then water containing 13 parts of sodium hydroxide was added thereto over 3 hours. The mixture was allowed to react at 55~60° C. for 2 hours. The reaction mixture was then acidified by adding 11 parts of hydrochloric acid and 30 parts of chloroform were added thereto, whereafter an organic layer (chloroform) was partitioned to obtain 35.6 g of 4-tetrahydroxyperfuryloxycarbitol-α-hydroxy benzeneacetic acid (yield: 93%).

Example 4

22.4 parts of 4-methoxycarbitoxy benzaldehyde was mixed with 19.6 parts of chloroform and 2.5 parts of benzyltriethylammonium chloride and the resulting mixture was heated to about 58° C., then water containing 13 parts of sodium hydroxide was added thereto over 5 hours. The mixture was allowed to react at 55~60° C. for 2 hours. The reaction mixture was then acidified by adding 11 parts of hydrochloric acid, whereafter an organic layer (chloroform) was partitioned to obtain 25.1 g of 4-methylcarbitoxy-α-hydroxy benzeneacetic acid (yield: 92%).

Examples 5~17

A variety of α-hydroxy benzeneacetic acid derivatives were synthesized in the same manner as in Example 1 except for using compounds as listed in TABLE 1 below instead of 4-propoxyethoxy benzaldehyde.

TABLE 1

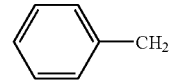

$D_1 = O, R_1 = R_3 - O - R_4$ (para-position)

| Example | $R_3$ | $R_4$ | A | Yield |
|---|---|---|---|---|
| 5 | $CH_2CH_2CH_2$ | 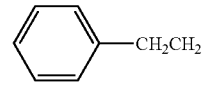 | H | 92% |
| 6 | $CH_2CH_2$ | 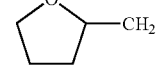 | H | 93% |
| 7 | $CH_2CH_2CH_2$ | $CH_3CH_2$ | H | 92% |
| 8 | $CH_2CH_2$ | 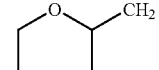 | H | 93% |
| 9 | $CH_2CH_2$ | 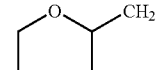 | H | 92% |
| 10 | $CH_2CH_2CH_2$ | $CH_3CH_2CH_2$ | H | 90% |
| 11 | $CH_2CH_2$ | $CH_3CH_2$ | H | 90% |
| 12 | $CH_2CH_2$ | 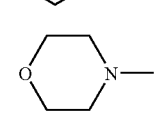 | H | 92% |
| 13 | $CH_2CH_2$ |  | H | 93% |
| 14 | $CH_2CH_2CH_2$ | $CH_3CH_2CH_2CH_2$ | H | 92% |

TABLE 1-continued

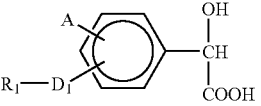

$D_1 = O, R_1 = R_3-O-R_4$ (para-position)

| Example | $R_3$ | $R_4$ | A | Yield |
|---------|-------|-------|---|-------|
| 15 | $CH_2CH_2$ | 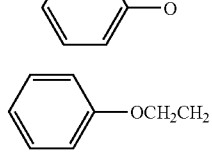 | H | 95% |
| 16 | $CH_2CH_2$ | 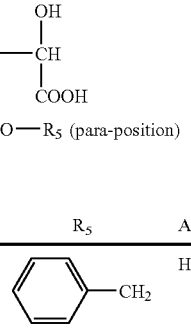 | H | 95% |
| 17 | $CH_2CH_2CH_2$ | $CH_3(CH)CH_3CH_2$ | H | 92% |

Examples 18~30

A variety of α-hydroxy benzeneacetic acid derivatives were synthesized in the same manner as in Example 1 except for using compounds as listed in TABLE 2 below instead of 4-propoxyethoxy benzaldehyde.

TABLE 2

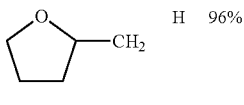

$D_1 = O, R_1 = R_3-O-R_4-O-R_5$ (para-position)

| Example | $R_3$ | $R_4$ | $R_5$ | A | Yield |
|---------|-------|-------|-------|---|-------|
| 18 | $CH_2CH_2$ | $CH_2CH_2$ | 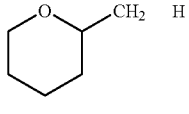 | H | 96% |
| 19 | $CH_2CH_2$ | $CH_2CH_2$ | $CH_3CH_2$ | H | 94% |
| 20 | $CH_2CH_2CH_2$ | $CH_2CH_2CH_2CH_2$ | $CH_3CH_2$ | H | 95% |
| 21 | $CH_2CH_2CH_2$ | $CH_2CH_2$ | 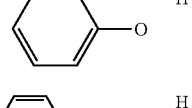 | H | 96% |
| 22 | $CH_2CH_2$ | $CH_2CH_2$ | 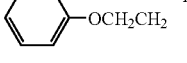 | H | 96% |
| 23 | $CH_2CH_2$ | $CH_2CH_2$ | $CH_3CH_2CH_2$ | H | 93% |
| 24 | $CH_2CH_2$ | $CH_2CH_2$ | $CH_3$ | H | 90% |
| 25 | $CH_2CH_2$ | $CH_2CH_2$ | 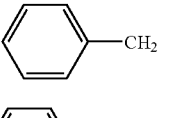 | H | 92% |
| 26 | $CH_2CH_2$ | $CH_2CH_2$ | 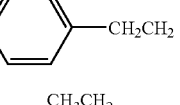 | H | 93% |
| 27 | $CH_2CH_2$ | $CH_2CH_2$ | $CH_3CH_2CH_2CH_2$ | H | 95% |

TABLE 2-continued

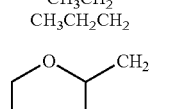

$D_1 = O, R_1 = R_3-O-R_4-O-R_5$ (para-position)

| Example | $R_3$ | $R_4$ | $R_5$ | A | Yield |
|---------|-------|-------|-------|---|-------|
| 28 | $CH_2CH_2$ | $CH_2CH_2$ | 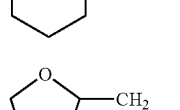 | H | 96% |
| 29 | $CH_2CH_2$ | $CH_2CH_2$ | 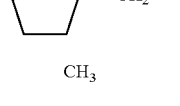 | H | 95% |
| 30 | $CH_2CH_2CH_2$ | $CH_2CH_2CH_2$ | $CH_3(CH)CH_3CH_2$ | H | 91% |

Examples 31~43

A variety of α-hydroxy benzeneacetic acid derivatives were synthesized in the same manners as in Example 1 except for using compounds as listed in TABLE 3 below instead of 4-propoxyethoxy benzaldehyde.

TABLE 3

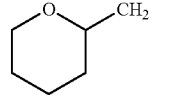

$D_1 = O, R_1 = R_3$ (para-position)

| Example | $R_3$ | A | Yield |
|---------|-------|---|-------|
| 31 | 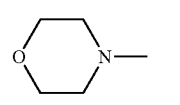 | H | 95% |
| 32 |  | H | 93% |
| 33 | $CH_3CH_2$ | H | 92% |
| 34 | $CH_3CH_2CH_2$ | H | 92% |
| 35 |  | H | 93% |
| 36 | | H | 96% |
| 37 | $CH_3$ | H | 90% |
| 38 | | H | 92% |
| 39 | | H | 93% |

TABLE 3-continued

![structure: R1—D1—(A)phenyl—CH(OH)COOH; D1 = O, R1 = R3 (para-position)]

| Example | R3 | A | Yield |
|---|---|---|---|
| 40 | CH₃CH₂O | H | 92% |
| 41 | C₆H₅—O | H | 95% |
| 42 | C₆H₅—OCH₂CH₂ | H | 95% |
| 43 | CH₃O | H | 92% |

Example 44

11 parts of the α-hydroxy benzeneacetic acid derivative, obtained in Example 1, and 6.8 parts of 5-hydroxy-2-oxo-3-phenyl-2,3-dihydro benzofuran were added to 148 parts of a mixed solvent of acetic acid and sulfuric acid (acetic acid: sulfuric acid=95:10) to carry out a condensation reaction at about 77° C. for 6 hours, then 7.44 parts of ammonium persulfate was added thereto to carry out an oxidation reaction at 100° C. for more than 1 hour while stirring. The reaction mixture was cooled to room temperature and then crystallized by adding 28.6 parts of methanol thereto. Crystals were filtered and washed with methanol and water several times to obtain 15.5 g of benzodifuranone-based dye compound, as represented in the below formula. $\lambda_{max}$=499 nm/CHCl₃

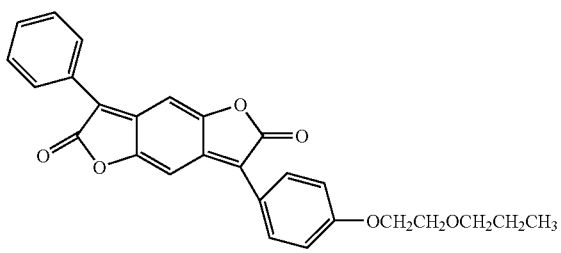

Example 45

7.0 parts of the α-hydroxy benzeneacetic acid derivative, obtained in Example 2, and 6.8 parts of 5-hydroxy-2-oxo-3-phenyl-2,3-dihydro benzofuran were added to a mixed solvent of chlorobenzene and sulfuric acid (chlorobenzene: 30 parts by weight, sulfuric acid: 1.5 parts by weight) to carry out a condensation reaction at about 77° C. for 7 hours, then 7.44 parts of ammonium persulfate was added thereto to carry out an oxidation reaction at 100° C. for more than 1 hour while stirring. The reaction mixture was cooled to room temperature and then crystallized by adding 28.6 parts of methanol thereto. Crystals were filtered and washed with methanol and water several times to obtain 10.2 g of benzodifuranone-based dye compound, as represented in the below formula $\lambda_{max}$=500 nm/CHCl₃

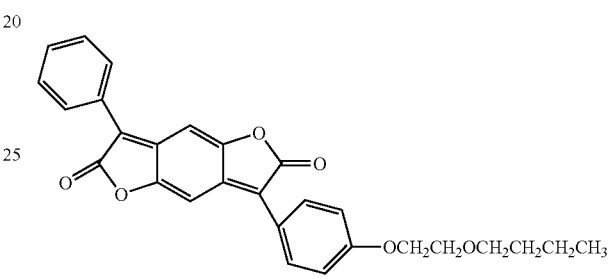

Example 46

12.24 parts of the α-hydroxy benzeneacetic acid derivative, obtained in Example 3, and 6.8 parts of 5-hydroxy-2-oxo-3-phenyl-2,3-dihydro benzofuran were added to a mixed solvent of chlorobenzene and sulfuric acid (chlorobenzene: 30 parts by weight, sulfuric acid: 2 parts by weight) to carry out a condensation reaction at about 77° C. for 7 hours, then 7.44 parts of ammonium persulfate was added thereto to carry out an oxidation reaction at 100° C. for more than 1 hour while sting. The reaction mixture was cooled to room temperature and then crystallized by adding 28.6 parts of methanol thereto. Crystals were filtered and washed with methanol and water several times to obtain 11.5 g of benzodifuranone-based dye compound, as represented in the below formula. $\lambda_{max}$=500 nm/CHCl₃

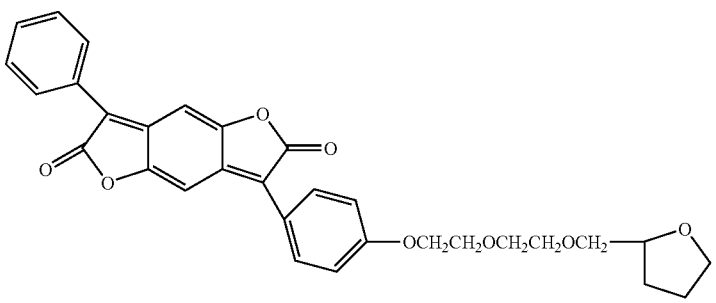

Example 47

6.7 parts of the α-hydroxy benzeneacetic acid derivative, obtained in Example 34, and 6.8 parts of 5-hydroxy-2-oxo-3-phenyl-2,3-dihydro benzofuran were added to a mixed solvent of o-dichlorobenzene and sulfuric acid (o-dichlorobenzene: 20 parts by weight, sulfuric acid: 2 parts by weight) to carry out a condensation reaction at about 77° C. for 7 hours, then 7.8 parts of chloranil was added thereto to carry out an oxidation reaction at 100° C. for more than 1 hour while stirring. The reaction mixture was cooled to room temperature and then crystallized by adding 28.6 parts of methanol thereto. Crystals were filtered and washed with methanol and water several times to obtain 8.9 g of benzodifuranone-based dye compound, as represented in the below formula $\lambda_{max}$=500 nm/CHCl$_3$

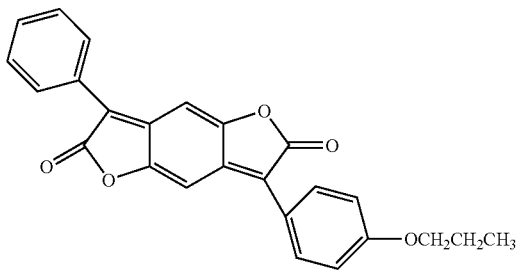

Example 48

7.6 parts of the O-hydroxy benzeneacetic acid derivative, obtained in Example 36, and 6.8 parts of 5-hydroxy-2-oxo-3-phenyl-2,3-dihydro benzofuran were added to a mixed solvent of o-dichlorobenzene and sulfuric acid (o-dichlorobenzene: 20 parts by weight, sulfuric acid: 2 parts by weight) to carry out a condensation reaction at about 77° C. for 7 hours, then 7.8 parts of chloranil was added thereto to carry out an oxidation reaction at 100° C. for more than 1 hour while stirring. The reaction mixture was cooled to room temperature and then crystallized by adding 28.6 parts of methanol thereto. Crystals were filtered and washed with methanol and water several times to obtain 9.9 g of benzodifuranone-based dye compound, as represented in the below formula $\lambda_{max}$=498 nm/CHCl$_3$

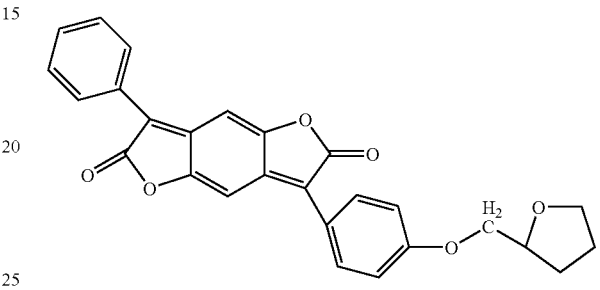

Examples 49-117

By using α-hydroxy benzeneacetic acid derivatives synthesized in the same manner as in Example 1, a variety of benzodifuranone-based dye compounds as listed in TABLE 4 below were synthesized in the same manner as in Example 44 and their colors were ascertained.

TABLE 4

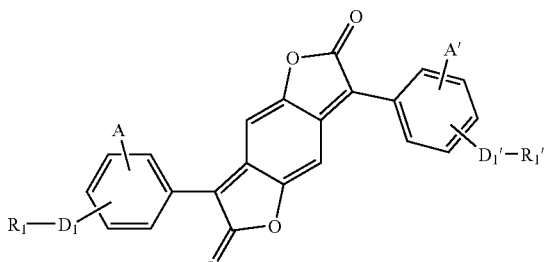

A = H; R$_1$ = R$_3$—D$_2$—R$_4$—D$_3$—R$_5$; D$_1$' = direct bond

| Example | R$_1$' | R$_3$ | D$_1$ | R$_4$ | A' | D$_2$ | R$_5$ | D$_3$ | Color CHCl$_3$ $\lambda_{max}$ (nm) |
|---|---|---|---|---|---|---|---|---|---|
| 50 | H | (CH$_2$)$_3$ | O | (CH$_2$)$_3$ | H | O | (CH$_2$)$_2$CH$_3$ | O | Red 500 |
| 51 | H | (CH$_2$)$_3$ | O | (CH$_2$)$_2$ | H | O | H | — | Red 500 |
| 52 | H | (CH$_2$)$_4$ | O | (CH$_2$)$_4$ | H | O | (CH$_2$)$_4$CH$_3$ | O | Red 500 |
| 53 | H | (CH$_2$)$_3$ | O | (CH$_2$)$_2$ | H | O | (CH$_2$)$_3$CH$_3$ | O | Red 500 |
| 54 | H | (CH$_2$)$_3$ | O | (CH$_2$)$_3$ | H | O | H | — | Red 500 |
| 55 | H | (CH$_2$)$_2$ | O | (CH$_2$)$_2$ | H | O | CH$_2$CH$_3$ | O | Red 501 |
| 56 | H | (CH$_2$)$_2$ | O | (CH$_2$)$_4$ | H | O | (CH$_2$)$_2$CH$_3$ | O | Red 500 |

TABLE 4-continued

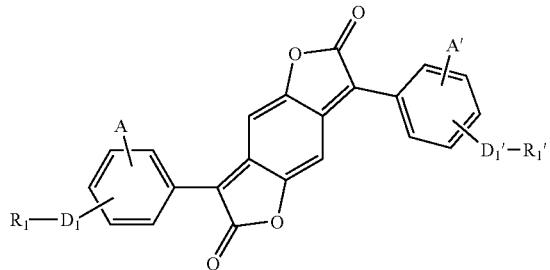

A = H; R$_1$ = R$_3$—D$_2$—R$_4$—D$_3$—R$_5$; D$_1$' = direct bond

| Example | R$_1$' | R$_3$ | D$_1$ | R$_4$ | A' | D$_2$ | R$_5$ | D$_3$ | Color CHCl$_3$ λ$_{max}$ (nm) |
|---|---|---|---|---|---|---|---|---|---|
| 57 | H | (CH$_2$)$_2$ | O | (CH$_2$)$_2$ | H | O | CH$_3$ | O | Red 501 |
| 58 | H | (CH$_2$)$_2$ | O | (CH$_2$)$_4$ | H | O | (CH$_2$)$_4$CH$_3$ | O | Red 501 |
| 59 | H | (CH$_2$)$_4$ | O | (CH$_2$)$_2$ | H | O | (CH$_2$)$_2$CH$_3$ | O | Red 500 |
| 60 | H | (CH$_2$)$_3$ | N | (CH$_2$)$_4$ | H | O | (CH$_2$)$_3$CH$_3$ | O | Blue |
| 61 | H | (CH$_2$)5 | O | — | H | — | H | — | Red 500 |
| 62 | H | (CH$_2$)$_2$ | O | (CH$_2$)$_2$ | H | O | (CH$_2$)$_3$CH$_3$ | O | Red 501 |
| 63 | H | (CH$_2$)$_4$ | O | (CH$_2$)$_4$ | H | O | H | — | Red 500 |
| 64 | H | (CH$_2$)$_3$ | O | (CH$_2$)$_2$ | H | O | (CH$_2$)$_4$CH$_3$ | O | Red 500 |
| 65 | H | (CH$_2$)$_2$ | O | (CH$_2$)$_3$ | H | O | (CH$_2$)$_2$CH$_3$ | O | Red 500 |
| 66 | H | (CH$_2$)$_4$ | N | (CH$_2$)$_4$ | H | S | CH$_2$CH$_3$ | S | Blue |
| 67 | H | (CH$_2$)$_2$ | O | (CH$_2$)$_2$ | H | O | (CH$_2$)$_2$CH$_3$ | O | Red 501 |
| 68 | H | (CH$_2$)$_2$ | O | (CH$_2$)$_2$ | H | S | (CH$_2$)$_3$CH$_3$ | N | Red 501 |
| 69 | H | (CH$_2$)$_2$ | O | (CH$_2$)$_2$ | H | N | (CH$_2$)$_2$CH$_3$ | O | Red 501 |
| 70 | H | (CH$_2$)$_3$ | O | (CH$_2$)$_3$ | H | O | morpholinyl | — | Red 501 |
| 71 | H | (CH$_2$)$_2$ | O | (CH$_2$)$_2$ | H | O | tetrahydrofurfuryl | O | Red 500 |
| 72 | H | (CH$_2$)$_3$ | O | (CH$_2$)$_2$ | H | O | tetrahydrofurfuryl | O | Red 500 |
| 73 | H | (CH$_2$)$_4$ | O | — | H | O | tetrahydrofurfuryl | — | Red 499 |
| 74 | H | (CH$_2$)$_2$ | O | — | H | — | morpholinyl | — | Red 501 |
| 75 | H | (CH$_2$)$_2$ | O | (CH$_2$)$_3$ | H | O | tetrahydropyranylmethyl | O | Red 499 |
| 76 | H | (CH$_2$)$_2$ | O | (CH$_2$)$_3$ | H | O | morpholinyl | — | Red 488 |

TABLE 4-continued

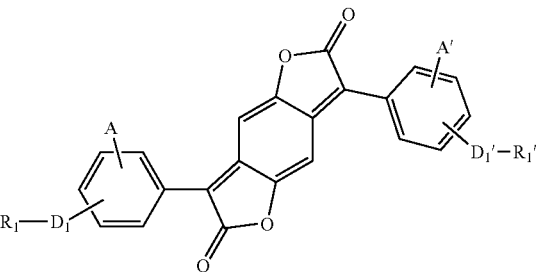

A = H; R₁ = R₃—D₂—R₄—D₃—R₅; D₁' = direct bond

| Example | R₁' | R₃ | D₁ | R₄ | A' | D₂ | R₅ | D₃ | Color CHCl₃ $\lambda_{max}$ (nm) |
|---------|-----|----|----|-----|-----|-----|------|-----|------|
| 77 | H | (CH₂)₃ | O | (CH₂)₂ | H | O | tetrahydropyran-2-yl-CH₂ | O | Red 500 |
| 78 | H | (CH₂)₃ | O | (CH₂)₃ | H | O | tetrahydrofuran-2-yl-CH₂ | O | Red 501 |
| 79 | H | (CH₂)₃ | O | (CH₂)₃ | H | O | tetrahydropyran-2-yl-CH₂ | O | Red 500 |
| 80 | H | (CH₂)₂ | O | (CH₂)₃ | H | O | tetrahydrofuran-2-yl-CH₂ | O | Red 500 |
| 81 | H | (CH₂)₂ | O | (CH₂)₂ | H | O | tetrahydropyran-2-yl-CH₂ | O | Red 500 |
| 82 | H | (CH₂)₃ | O | — | H | O | tetrahydrofuran-2-yl-CH₂ | O | Red 500 |
| 83 | H | (CH₂)₂ | O | (CH₂)₂ | H | O | morpholin-4-yl | — | Red 500 |
| 84 | H | (CH₂)₂ | S | (CH₂)₄ | H | O | tetrahydropyran-2-yl-CH₂ | O | Red 500 |
| 85 | H | (CH₂)₂ | O | (CH₂)₄ | H | O | morpholin-4-yl | — | Red 500 |
| 86 | H | (CH₂)₃ | O | (CH₂)₄ | H | O | tetrahydrofuran-2-yl-CH₂ | O | Red 499 |
| 87 | H | (CH₂)₃ | O | (CH₂)₄ | H | O | tetrahydropyran-2-yl-CH₂ | O | Red 501 |

TABLE 4-continued

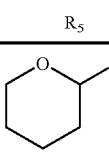

A = H; R₁ = R₃—D₂—R₄—D₃—R₅; D₁' = direct bond

| Example | R₁' | R₃ | D₁ | R₄ | A' | D₂ | R₅ | D₃ | Color CHCl₃ $\lambda_{max}$ (nm) |
|---|---|---|---|---|---|---|---|---|---|
| 88 | H | (CH₂)₄ | O | (CH₂)₄ | H | N | tetrahydropyran-2-yl-CH₂ | O | Red 500 |
| 89 | H | (CH₂)₄ | O | (CH₂)₄ | H | O | HN-piperazinyl | — | Red 500 |
| 90 | H | (CH₂)₃ | O | (CH₂)₄ | H | O | morpholino | — | Red 500 |
| 91 | CH₃ | (CH₂)₂ | O | (CH₂)₂ | H | O | CH₃ | O | Blue red 506 |
| 92 | CH₃ | (CH₂)₂ | O | (CH₂)₂ | H | O | (CH₂)₃CH₃ | O | Blue red 507 |
| 93 | CH₃ | (CH₂)₂ | O | (CH₂)₂ | H | S | (CH₂)₂CH₃ | O | Blue red 507 |
| 94 | CH₃ | (CH₂)₂ | O | (CH₂)₂ | H | O | CH₂CH₃ | O | Blue red 507 |
| 95 | CH₃ | (CH₂)₂ | O | (CH₂)₂ | H | O | morpholino | — | Blue red 507 |
| 96 | CH₃ | (CH₂)₂ | O | (CH₂)₄ | H | O | tetrahydropyran-2-yl-CH₂ | O | Blue red 505 |
| 97 | CH₃ | (CH₂)₂ | O | (CH₂)₄ | H | O | morpholino | — | Blue red 503 |
| 98 | CH₃ | (CH₂)₃ | O | (CH₂)₂ | H | O | tetrahydrofuran-2-yl-CH₂ | O | Blue red 509 |
| 99 | CH₃ | (CH₂)₃ | O | (CH₂)₂ | H | O | tetrahydropyran-2-yl-CH₂ | O | Blue red 507 |
| 100 | CH₃ | (CH₂)₃ | O | (CH₂)₂ | H | O | morpholino | — | Blue red 509 |

TABLE 4-continued

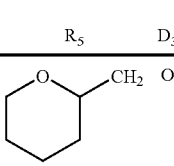

A = H; R₁ = R₃—D₂—R₄—D₃—R₅; D₁' = direct bond

| Example | R₁' | R₃ | D₁ | R₄ | A' | D₂ | R₅ | D₃ | Color CHCl₃ $\lambda_{max}$ (nm) |
|---|---|---|---|---|---|---|---|---|---|
| 101 | CH₃ | (CH₂)₂ | O | (CH₂)₃ | H | O | 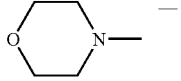 | O | Blue red 506 |
| 102 | CH₃ | (CH₂)₂ | O | (CH₂)₃ | H | S | 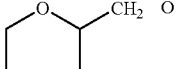 | — | Blue red 502 |
| 103 | CH₃ | (CH₂)₄ | O | (CH₂)₄ | H | O | 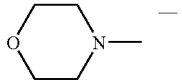 | O | Blue red 506 |
| 104 | CH₃ | (CH₂)₄ | O | (CH₂)₄ | H | O | 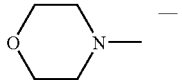 | — | Blue red 506 |
| 105 | CH₃ | (CH₂)₃ | O | (CH₂)₄ | H | O | 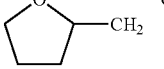 | — | Blue red 507 |
| 106 | CH₃ | (CH₂)₃ | O | (CH₂)₃ | H | O | 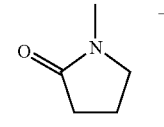 | O | Blue red 507 |
| 107 | CH₃ | (CH₂)₃ | O | (CH₂)₃ | H | O | 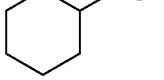 | — | Blue red 506 |
| 108 | CH₃ | (CH₂)₃ | O | (CH₂)₃ | H | O | 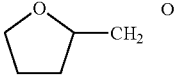 | O | Blue red 506 |
| 109 | CH₃ | (CH₂)₂ | O | (CH₂)₂ | H | O | 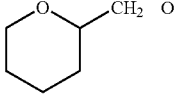 | O | Blue red 504 |
| 110 | CH₃ | (CH₂)₂ | O | (CH₂)₂ | H | S | 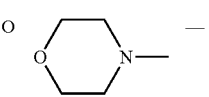 | O | Blue red 508 |
| 111 | CH₃ | (CH₂)₃ | O | (CH₂)₃ | H | O |  | — | Blue red 504 |

TABLE 4-continued

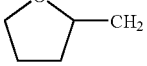

A = H; R₁ = R₃—D₂—R₄—D₃—R₅; D₁' = direct bond

| Example | R₁' | R₃ | D₁ | R₄ | A' | D₂ | R₅ | D₃ | Color CHCl₃ $\lambda_{max}$ (nm) |
|---|---|---|---|---|---|---|---|---|---|
| 112 | CH₃ | (CH₂)₂ | O | (CH₂)₄ | H | O | 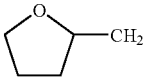 | O | Blue red 504 |
| 113 | CH₃ | (CH₂)₃ | O | (CH₂)₄ | H | N | 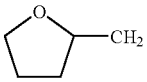 | O | Blue red 511 |
| 114 | CH₃ | (CH₂)₄ | O | (CH₂)₄ | H | O | 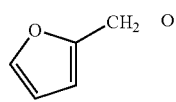 | O | Blue red 507 |
| 115 | H | (CH₂)₂ | O | (CH₂)₂ | H | O |  | O | Blue red 488 |
| 116 | H | (CH₂)₃ | O | (CH₂)₂ | H | O | 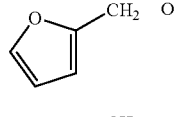 | O | Blue red 487 |
| 117 | H | (CH₂)₂ | O | (CH₂)₃ | H | O | 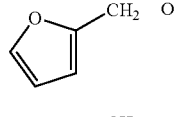 | O | Blue red 489 |

Note: "—" means a direct bond

These Examples show only exemplary compounds according to the present invention and further various compounds can also be prepared in the scope of the present invention.

Experimental Example 1

Each of 2 parts of the benzodifuranone-based dye compounds, obtained in some examples, respectively, was finely pulverized in an aqueous medium with the aid of 6 parts of naphthalenesulfonic acid-formaldehyde condensate and 100 parts of water was added thereto to prepare a liquid dye dispersion, which was then spray-dried to form dye powders. A polyester cloth was dipped in a dye bath containing 0.6 parts of the dye powders, then dyeing was carried out at 132° C. under high pressure for 60 minutes. As cloths for dyeing, were used cloths of polyester fibers, polyester/nylon micro fibers, and polyester/wool blends, respectively. The dye cloth was dipped in 3000 parts of water containing 3 parts of sodium hydroxide, 3 parts of hydrogen sulfide and 3 parts of amphoteric surfactant to be subjected to reduction-rinsing treatment at 85° C. for 10 minutes, followed by washing with water and drying. The resulting dyed cloth was dipped in a padding liquor containing softening agent (10 g/L, Edunine V Fluid® ICI) and antistatic agent (5 g/L, Edunine AT-30® ICI) and then squeezed uniformly at a pick-up rate of 80%. This procedure was repeated once more, then the cloth was pre-dried at 90° C. for 2 minutes and subjected to heat setting at 170° C. for 1 minute, followed by post treatment.

The dye fixing rate of the dyed cloths obtained after the post-treatment was measured by a computer color matching machine (CCM) and several fastness properties thereof were also measured in accordance with the procedures as follows, respectively, the results of which are disclosed in TABLE 5 below.

(1) Washing fastness: a dyed cloth and a white cloth were dipped in a solution containing detergent (5 g/L) and soda ash (2 g/L) and stirred at 60° C. for 30 minutes using ten steel balls, then the change of color in the dyed cloth and the contamination of the white cloth were measured;

(2) Light fastness: a dyed cloth was tested for 20 hours using a fading testing device (xenon lamp) to measure the change of color thereof;

(3) Sublimation fastness: a dyed cloth and a white cloth, which were overlapped with one another, were tested at 180° C. for 30 seconds using a sublimation testing device (heat plate), while being compressed, to measure the migration degree of dye to the white cloth.

TABLE 5

| Example | Dye fixing rate | | | Fastness | | |
|---|---|---|---|---|---|---|
| | Polyester fiber | Polyester/ Nylon micro fiber | Polyester/ Wool fiber blend | Light | Sublimation | Washing |
| 44 | Δ | X | Δ | ○ | Δ | ○ |
| 46 | ○ | ○ | ○ | ◎ | ○ | ◎ |
| 47 | X | X | X | Δ | X | ○ |
| 48 | ◎ | Δ | ◎ | ◎ | Δ | ◎ |
| 55 | Δ | X | Δ | ◎ | Δ | ◎ |
| 57 | Δ | X | Δ | ◎ | Δ | ◎ |
| 62 | ◎ | ◎ | ◎ | ◎ | ◎ | ◎ |

Note:
X = bad, Δ = not bad, ○ = good, ◎ = excellent

From the test results, the cloths dyed by most benzodifuranone-based dye compounds were good in the washing fastness property but showed differences in the dye fixing rate (leveling property) and other fastness properties. For example, the benzodifuranone-based dye compound of Example 47, which is a representative dye compound for sport-wares requiring a good washing fastness property, failed to show a good dye fixing rate and light and sublimation fastness properties in comparison with compounds of other Examples. On the other hand, the dye compounds of Example 46 and 62 showed good effects in all fastness properties and also showed an excellent dye fixing rate to micro fibers, fiber blends, etc.

Experimental Example 2

Each of 2.6 parts of the benzodifuranone-based compounds, obtained in Example 1, was finely pulverized in an aqueous medium with the aid of 6.4 parts of lignin sulfonic acid to prepare dye powders, which were then added to a mixture containing 70 parts of hot water and 60 parts of an emulsion paste having the composition as in TABLE 6 below to prepare a printing paste.

TABLE 6

| Components | Content (part by weight) |
|---|---|
| Lamitex M | 524.6 |
| Sorbitol C5 | 10.5 |
| Sodiumhydrophosphate | 5.0 |
| Lyoprint A/R | 5.0 |
| Water | 950.9 |

A polyester cloth was printed with the printing paste obtained above, pre-dried and steamed at 170° C. for 7 minutes. The heat-treated, dyed cloth was tested to measure several fastness properties in the same manner as in Experimental example 1, which showed very similar results to those of Experimental example 1.

Experimental Example 3

By using the compounds of Examples 46, 48 and 62 among compounds used in Experimental example 1, the following experiment was carried out. To a dispersion solution containing 20 parts of each compound, 1.1 parts of acetic acid and 4.8 parts of sodium acetate were added and other dye compounds were added thereto at the mixing ratios as listed in TABLE 7 below, then 3000 parts of water were added to prepare dye solutions. Polyester cloths were dyed with these dye solutions at the same manner as in Experimental example 1, then pH dependency, stability of dye solution, and fastness of dyed cloths were measured and the results thereof are disclosed in TABLE 7, below.

The pH dependency was measured by confirming whether the color and dye fixing rate of a dyed cloth are stable when dyeing is performed at a varying pH of dye solution from weak acid to alkali condition. The stability of dye solution was measured by confirming whether the color and dye fixing rate of dyed cloth are changed when dyeing is performed using compounds after storage for a long time. The fastness properties were measured at the same manner as in Example 1.

TABLE 7

| Other dye compounds | Mixing ratio | pH dependency | Stability of dye solution | Fastness | |
|---|---|---|---|---|---|
| | | | | Light | Washing |
| Red 60 | 0.9 | ○ | ○ | ○ | ◎ |
| Red 146 | 0.2 | ○ | ○ | ○ | ◎ |
| Red 127 | 0.3 | ○ | ○ | ◎ | ◎ |
| Red 92 | 0.6 | ◎ | ◎ | ◎ | ○ |

Note:
○ = good, ◎ = excellent
Mixing ratio: the weight of a particular dye compound (other dye compound)/the weight of composition As seen in TABLE 7, the benzodifuranone-based compound according to the present invention exhibits excellent properties even when used together with other dye compounds.

Experimental Example 4

The compounds of Examples 46, 48 and 62, respectively, were mixed with the dye compound of the below formula to prepare a dye composition then the fastnesses of dyed products thereof were measured in the same manner as in Experimental example 1. The mixing ratio of both dye components was 1:1 (by weight). The results are disclosed in TABLE 8 below.

TABLE 8

$$\begin{array}{c}\text{structure with thiophene ring bearing } Q_1, Q_2, Q_3 \text{ substituents, linked via } N=N \text{ to a phenyl ring bearing } P_3, P_4 \text{ substituents, and } N(P_1)(P_2)\end{array}$$

| $P_1$ | $P_2$ | $P_3$ | $P_4$ | $Q_1$ | $Q_2$ | $Q_3$ | Fastness | |
|---|---|---|---|---|---|---|---|---|
| | | | | | | | Light | Washing |
| $C_2H_5$ | $C_2H_4CN$ | $CH_3$ | H | CN | H | $NO_2$ | ◎ | ◎ |
| $C_2H_5$ | $C_2H_4OCH_3$ | $CH_3$ | H | CN | H | $NO_2$ | ◎ | ◎ |

As seen in TABLE 8 above, the benzodifuranone-based dye compound according to the present invention exhibits excellent fastness properties even when used together with the compound of the above formula.

Experimental Example 5

In order to see the dyeability to micro fibers depending upon the number of carbon atoms present in a carbitoxy group(s) of benzodifuranone-based compound according to the present invention, compounds as listed in TABLE 9 below were synthesized at the same manner as in the above Examples, then the experiment of Experimental example 1 was repeated to micro fibers (1%). The results are disclosed in TABLE 9 below.

TABLE 9

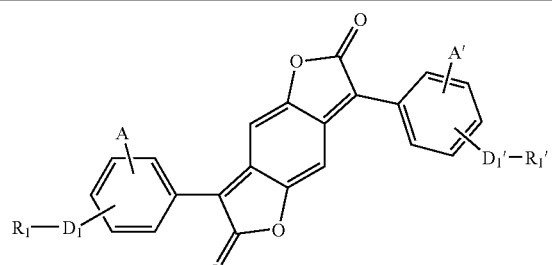

A, A', $R_1'$ = H; $D_1$ = O; $D_1'$ = direct bond; $R_1$ = $(CH_2)_2$—O—$(CH_2)_2$—O—$R_5$

| $R_5$ | Dye fixing rate | Fastness | | |
|---|---|---|---|---|
| | | Washing | Sublimation | Light |
| $CH_3$ | Δ | ◎ | ◎ | Δ |
| $CH_2CH_3$ | Δ | ◎ | ◎ | Δ |
| $(CH_2)_2CH_3$ | — | — | — | — |
| $(CH_2)_3CH_3$ | ◎ | ◎ | ◎ | ◎ |
| $(CH_2)_4CH_3$ | ○ | ○ | ○ | Δ |

As seen in TABLE 9 above, it was ascertained that a compound having the butoxy carbitoxy group of four carbon atoms ("butoxy carbitol compound") exhibits an unexpectedly superior properties to compounds having other carbitoxy groups in dyeing to micro fibers. Especially, in terms of the dye fixing rate, the butoxy carbitol compound exhibited at least 2 times better effect than methoxy and ethoxy carbitol compounds and also at least ½ times better effect than a pentoxy carbitol compound. It should be noted that such result is not known yet and was first found by the inventors of the present invention. As a result, we found in the art that the butoxy carbitol compound is a dye compound very useful in dyeing to micro fibers. On the other hand, the propoxy carbitol compound cannot be used as a dye compound because crystallization is not achieved after synthesis thereof.

Experimental Example 6

In order to confirm that the benzodifuranone-based compound according to the present invention can be used as a coloring agent for color filters, a paste for electrical laminate coating was prepared using the compounds of Examples 46, 48 and 62, respectively, by a method as described in Korean Laid-open Patent No. 2000-56622, then a relevant evaluation experiment was performed according to a method as described in U.S. Pat. No. 5,645,970. The result is disclosed in TABLE 9 below.

TABLE 9

| Component | Content (part by weight) | | |
|---|---|---|---|
| Anionic polyester resin | 95.0 | 95.0 | 95.0 |
| Melamine resin (Nikarakku MX-40) | 8.0 | 8.0 | 8.0 |
| 2-ethoxy butanol ethyl ether | 25.0 | 25.0 | 25.0 |
| 2-ethoxy ethanol ethyl ether | 5.0 | 5.0 | 5.0 |
| Neobutanol | 18.0 | 18.0 | 18.0 |
| Triethylamine | 2.5 | 2.5 | 2.5 |
| Desalted water | 813.5 | 813.5 | 813.5 |
| Phthalocyanine Blue (SR 1500) | 5.0 | — | — |
| Phthalocyanine Green (SAX) | — | 5.0 | — |
| Benzodifuranone-based compound (Example 46, etc.) | — | — | 5.0 |
| Total | 1000 | 1000 | 1000 |

From the experimental result it was ascertained that where the benzodifuranone-based compound according to the present invention is used in preparation of a color filter in which an electrical laminate color coating, containing an anionic resin of a low acidity, is used, and a high freedom degree in the pattern phenomenon and wide process window are obtained, and a color filter having a large surface can be produced at a very high yield.

Experimental Example 7

In order to confirm that the benzodifuranone-based compound according to the present invention can also be used as a coloring agent for molding resins, the following experiment was conducted.

First, 500 g of general polyester resin, 0.1 g of the compound of Example 46, 48 or 62, and 1.0 g of $TiO_2$ were put in a polyester bag and mixed, then injected through an injection molding machine gradually set to about 235, 225 and 190° C. to produce a plurality of chips.

In addition, 500 g of ABS resin, 0.2 g of the compound of Example 46, 48 or 62, and 2.0 g of $TiO_2$ were put in a polyethylene bag and mixed, then injected through an injection molding machine gradually set to about 240, 230 and 190° C. to produce a plurality of chips.

The color of these chips was measured by CCM, and the result showed that the above compounds are suitable for coloring of these resins.

Experimental Example 8

In order to confirm that the benzodifuranone-based compound according to the present invention can be as a coloring agent for color tonors, fine particles were prepared using the compound of Example 46, 48 or 62 by a method as described in Korean Laid-open Patent No. 2001-20439. These fine particles were tested to see a possibility of being used as color tonors, an excellent result was obtained.

In addition, an ink composition was prepared using the same compound and tested. Likewise, an excellent result was obtained.

INDUSTRIAL APPLICABILITY

According to the preparation process of the present invention, an α-hydroxy benzeneacetic acid derivative can be readily prepared at high purity and yield without using toxic materials or producing toxic by-products. As synthesized by using such a α-hydroxy benzeneacetic acid derivative as a precursor, some novel benzodifuranone-based dye compounds have excellent fastness properties, dye fixing rate and leveling property to general synthetic fiber materials such as polyester fibers and their blends with other fibers, especially to micro fibers, and also can be used as a coloring agent for plastic resins, color tonors, color filters, etc.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. A compound of Formula (IV)

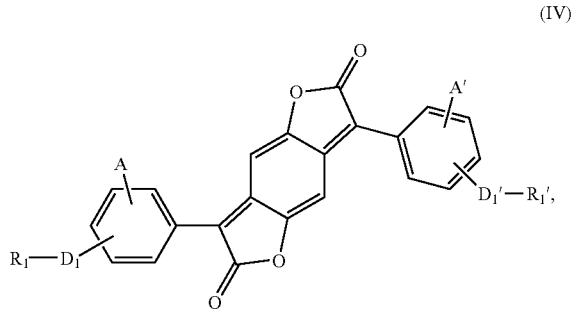

(IV)

wherein
A is hydrogen, halogen, substituted or unsubstituted $C_1$-$C_6$ alkyl, or substituted or unsubstituted $C_1$-$C_6$ alkoxy group;
$D_1$ is —O—, —S—, —$SO_2$— or —N(—$R_2$)—, wherein $R_2$ is hydrogen, or substituted or unsubstituted $C_1$-$C_6$ alkyl group;
$R_1$ is

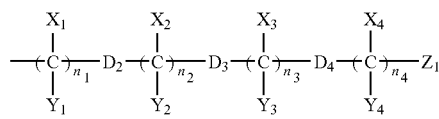

wherein
$D_2$ and $D_3$ are each independently —O—, —S— or —N(—$R_2$)—, wherein $R_2$ is the same as above;
$D_4$ is a direct bond, —O—, —S— or —N(—$R_2$)—, wherein $R_2$ is the same as above;
$X_1, X_2, X_3, X_4, Y_1, Y_2, Y_3$ and $Y_4$ are each independently hydrogen, halogen, or substituted or unsubstituted $C_1$-$C_6$ alkyl group;
$Z_1$ is an unsubstituted $C_3$-$C_6$ alkyl;
$n_1$ to $n_3$ are each independently an integer of 1~6;
$n_4$ is 0 or an integer of 1~6;
A' is hydrogen, halogen, substituted or unsubstituted $C_1$-$C_6$ alkyl, or substituted or unsubstituted $C_1$-$C_6$ alkoxy group;
$D_1'$ is a direct bond, —O—, —S—, —$SO_2$— or —N(—$R_2$)—, wherein $R_2$ is hydrogen, or substituted or unsubstituted $C_1$-$C_6$ alkyl group;
$R_1'$ is hydrogen, substituted or unsubstituted $C_1$-$C_6$ alkyl, substituted or unsubstituted $C_4$-$C_7$ cyclic or heterocyclic group, substituted or unsubstituted aromatic group, or

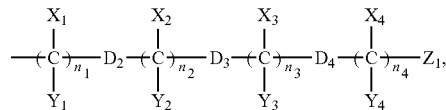

wherein
$D_2, D_3$ and $D_4$ are each independently a direct bond, —O—, —S— or —N(—$R_2$)—, wherein $R_2$ is the same as above;
$X_1, X_2, X_3, X_4, Y_1, Y_2, Y_3$ and $Y_4$ are each independently hydrogen, halogen, or substituted or unsubstituted $C_1$-$C_6$ alkyl group;
$Z_1$ is an unsubstituted $C_1$-$C_6$ alkyl;
$n_1$ is an integer of 1~6;
$n_2$ to $n_4$ are each independently 0 or an integer of 1~6, provided that when $n_2$ is 0, at least one of $D_2$ and $D_3$ is a direct bond; when $n_3$ is 0, at least one of $D_3$ and $D_4$ is a direct bond; and when $n_2$ and $n_3$ are simultaneously 0, $D_3$ is a direct bond and also at least one of $D_2$ and $D_4$ is a direct bond.

2. The compound of formula (IV) according to claim 1, wherein $D_1, D_2$ and $D_3$ are —O—.

3. The compound of formula (IV) according to claim 1, wherein $D_4$ is a direct bond and $n_4$ is 0.

4. The compound according to claim 1, wherein $n_1$ and $n_2$ are 2, respectively.

5. The benzodifuranone-based dye compound according to claim 1, wherein $n_3$ is 1, $D_4$ is a direct bond, $n_1$ is 0 and $Z_1$ denotes n-propyl.

6. The benzodifuranone-based dye compound according to claim 1, wherein A' is hydrogen, $D_1'$ is a direct bond, and $R_1'$ is hydrogen.

7. A method of dyeing hydrophobic fiber materials using the benzodifuranone-based dye compound according to claim 1.

8. The method according to claim 7, wherein the hydrophobic fiber materials are polyester fibers, polyester micro fibers, their blends with other fibers, or hydrophobic fiber-based weave cloths.

9. A method of using the benzodifuranone-based compound according to claim 1 as a coloring agent for plastic resins, color filters or color tonors.

10. A mixture of at least one dye of the formula (IV)

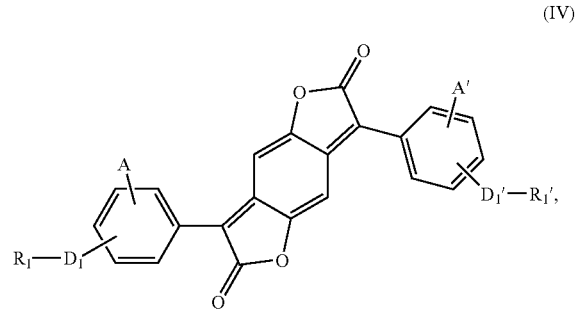

(IV)

wherein
A is hydrogen, halogen, substituted or unsubstituted $C_1$-$C_6$ alkyl, or substituted or unsubstituted $C_1$-$C_6$ alkoxy group;

$D_1$ is —O—, —S—, —SO$_2$— or —N(—R$_2$)—, wherein R$_2$ is hydrogen, or substituted or unsubstituted C$_1$-C$_6$ alkyl group;

R$_1$ is

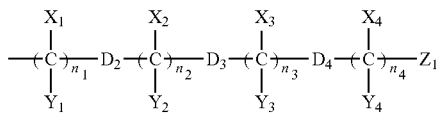

wherein
D$_2$ and D$_3$ re each independently —O—, —S— or —N(—R$_2$)—, wherein R$_2$ is the same as above;
D$_4$ is a direct bond, —O—, —S— or —N(—R$_2$)—, wherein R$_2$ is the same as above;
X$_1$, X$_2$, X$_3$, X$_4$, Y$_1$, Y$_2$, Y$_3$ and Y$_4$ are each independently hydrogen, halogen, or substituted or unsubstituted C$_1$-C$_6$ alkyl group;
Z$_1$ is an unsubstituted C$_3$-C$_6$ alkyl;
n$_1$ to n$_3$ are each independently an integer of 1~6;
n$_4$ is 0 or an integer of 1~6;
A' is hydrogen, halogen, substituted or unsubstituted C$_1$-C$_6$ alkyl, or substituted or unsubstituted C$_1$-C$_6$ alkoxy group;
D$_1$' is a direct bond, —O—, —S—, —SO$_2$— or —N(—R$_2$)—, wherein R$_2$ is hydrogen, or substituted or unsubstituted C$_1$-C$_6$ alkyl group;
R$_1$' is hydrogen, substituted or unsubstituted C$_1$-C$_6$ alkyl, substituted or unsubstituted C$_4$-C$_7$ cyclic or heterocyclic group, substituted or unsubstituted aromatic group, or

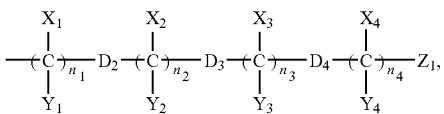

wherein
D$_2$, D$_3$ and D$_4$ are each independently a direct bond, —O—, —S— or —N(—R$_2$)—, wherein R$_2$ is the same as above;
X$_1$, X$_2$, X$_3$, X$_4$, Y$_1$, Y$_2$, Y$_3$ and Y$_4$ are each independently hydrogen, halogen, or substituted or unsubstituted C$_1$-C$_6$ alkyl group;
Z$_1$ is an unsubstituted C$_1$-C$_6$ alkyl;
n$_1$ is an integer of 1~6;
n$_2$ to n$_4$ are each independently 0 or an integer of 1~6, provided that when n$_2$ is 0, at least one of D$_2$ and D$_3$ is a direct bond; when n$_3$ is 0, at least one of D$_3$ and D$_4$ is a direct bond; and when n$_2$ and n$_3$ are simultaneously 0, D$_3$ is a direct bond and also at least one of D$_2$ and D$_4$ is a direct bond;

together with at least one dye of the formulae (VI)

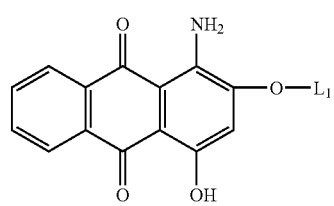

wherein
L$_1$ is C$_1$-C$_6$ alkyl, phenyl, or C$_1$-C$_4$ alkoxyphenylsulfonyl group, (VII)

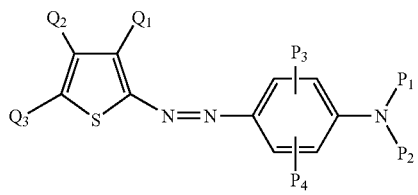

wherein
P$_1$ and P$_2$ are each independently C$_1$-C$_6$ alkyl, phenyl, C$_1$-C$_4$ alkoxyphenylsulfonyl, cyanoethyl, cyanopropyl, phenoxyethyl, C$_1$-C$_6$ alkoxyethyl or alkoxypropyl, or C$_1$-C$_6$ alkoxy carbitoxy group; and
P$_3$, P$_4$, Q$_1$, Q$_2$ and Q$_3$ are each independently hydrogen, C$_1$-C$_4$ alkyl, especially methyl, hydroxy, acetyl amide, propionyl amide, butylcarbonyl amide, C$_1$-C$_4$ alkoxy, nitro or a cyano group, (VIII)

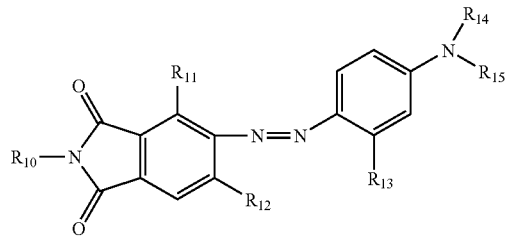

wherein
R$_{10}$ is C$_1$-C$_6$ alkyl, especially C$_1$-C$_4$ alkyl;
R$_{11}$ and R$_{12}$ independently of one another are hydrogen, cyano or halogen, especially chlorine or bromine;
R$_{13}$ is C$_1$-C$_4$ alkyl, especially methyl or ethyl, hydroxy, halogen, especially bromine or chlorine, —NH—SO$_2$—R$_{16}$ or —NH—CO—R$_{17}$, wherein R$_{16}$ is C$_1$-C$_4$ alkyl, and R$_{16}$ is C$_1$-C$_4$ alkyl or C$_1$-C$_4$alkoxy-C$_1$-C$_4$ alkyl;
and R$_{14}$ and R$_{15}$ independently of one another are C$_1$-C$_6$ alkyl which is unsubstituted or substituted by one or more hydroxy groups, halogen atoms, C$_1$-C$_4$ alkoxy groups, C$_2$-C$_8$ alkoxyalkoxy groups, C$_1$-C$_4$alkyl-COO— groups or C$_1$-C$_4$allyl-OCO— groups, (IX)

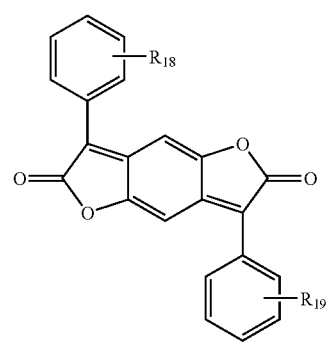

wherein
R$_{18}$ and R$_{19}$ independently of one another are hydrogen, C$_1$-C$_6$ alkyl, especially methyl, ethyl or butyl, C$_1$-C$_6$alkoxy, especially methoxy, ethoxy and n-propoxy, C$_1$-C$_4$alkoxy-C$_1$-C$_4$alkoxycarbonyl-C$_1$-C$_4$alkoxy groups, or $R_{18}$ and $R_{19}$ are heterocyclyl-$C_1$-$C_4$alkoxy groups, especially tetrahydrofuranyl-$C_1$-$C_4$alkoxy groups,

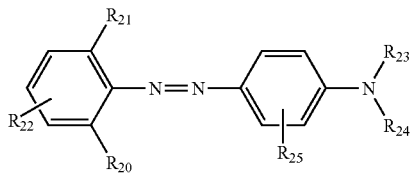
(X)

wherein
- $R_{20}$ and $R_{21}$ are each independently of one another hydrogen, halogen, especially chlorine or bromine or cyano;
- $R_{22}$ is $C_1$-$C_6$ alkyl, especially methyl, nitro or $C_1$-$C_4$ alkoxy;
- $R_{23}$ and $R_{24}$ are each independently of one another $C_1$-$C_6$ alkyl or $C_1$-$C_4$ alkoxy-$C_1$-$C_4$alkyl; and
- $R_{25}$ is $C_1$-$C_4$ alkyl, especially methyl or ethyl, hydroxy, halogen, especially bromine or chlorine, —NH—SO$_2$—$R_{16}$ or —NH—CO—$R_{17}$, wherein $R_{16}$ and $R_{17}$ have the meaning given under formula VIII,

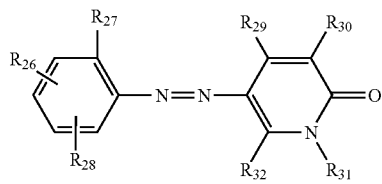
(XI)

wherein
- $R_{26}$ is $C_1$-$C_6$ alkyl, nitro or $C_1$-$C_6$ alkoxy;
- $R_{27}$ is cyano, nitro or halogen, especially bromine or chlorine;
- $R_{28}$ is hydrogen, cyano, intro or halogen, especially bromine or chlorine;
- $R_{29}$ is $C_1$-$C_6$ alkyl, especially methyl;
- $R_{30}$ is cyano;
- $R_{31}$ is $C_1$-$C_6$ alkyl, $C_1$-$C_4$ alkoxy-$C_1$-$C_4$ alkyl, phenyl-$C_1$-$C_4$ alkyl or phenoxy-$C_1$-$C_4$ alkyl; and
- $R_{32}$ is hydrogen or hydroxy, or

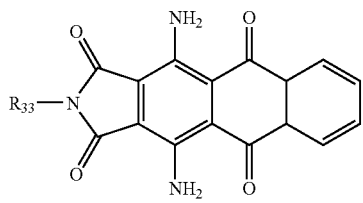
(XII)

wherein
- $R_{33}$ is $C_1$-$C_6$ alkyl, especially $C_2$-$C_4$ alkyl, unsubstituted or substituted by $C_1$-$C_4$ alkoxy, especially $C_1$-$C_2$ alkoxy, or $C_1$-$C_4$ alkoxy-$C_1$-$C_4$ alkoxy, especially $C_1$-$C_2$ alkoxy-$C_2$-$C_3$ alkoxy.

\* \* \* \* \*